(12) United States Patent
Fritz et al.

(10) Patent No.: US 6,815,177 B2
(45) Date of Patent: Nov. 9, 2004

(54) USE OF YLQF, YQEG, YYBQ, AND YSXC, ESSENTIAL BACTERIAL GENES AND POLYPEPTIDES

(75) Inventors: Christian Fritz, Natick, MA (US); Philip Youngman, Boston, MA (US); Luz-Maria Guzman, Boston, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/423,330

(22) Filed: Apr. 25, 2003

(65) Prior Publication Data

US 2003/0228643 A1 Dec. 11, 2003

Related U.S. Application Data

(62) Division of application No. 10/023,528, filed on Dec. 17, 2001, now Pat. No. 6,638,729, which is a division of application No. 09/222,939, filed on Dec. 30, 1998, now Pat. No. 6,372,448.

(51) Int. Cl.[7] .................................................. C12Q 1/18
(52) U.S. Cl. .............................. 435/32; 435/4; 435/7.1; 435/7.2; 435/7.32
(58) Field of Search .............................. 435/32, 4, 7.1, 435/7.2, 7.32

(56) References Cited

PUBLICATIONS

Bowman et al.; "The nucleotide sequence of *Saccharomyces cerevisiae* chromosome XIII"; NATURE, vol. 387: Issue No. 6632S Supplement to Nature; pp. 90–93 (May 29, 1997).

Bussey et al.; "The nucleotide sequence of *Saccharomyces cerevisiae* chromosome XVI"; NATURE, vol. 387; Issue No. 6632S Supplement to Nature; pp. 103–105 (May 29, 1997).

Blattner et al.; "The Complete Genome Sequence of *Escherichia coli* K–12"; SCIENCE, vol. 277; pp. 1453–1462; Sep. 5, 1997.

Churcher et al.; "The nucleotide sequence of *Saccharomyces cerevisiae* chromosome IX"; NATURE, vol. 387; Issue No. 6632S Supplement to Nature; pp. 84–87 (May 29, 1997).

Dujon et al.; "The nucleotide sequence of *Saccharomyces cerevisiae* chromosome XV"; NATURE, vol. 387; Issue No. 6632S Supplement to Nature; pp. 98–102 (May 29, 1997).

Johnston et al.; "The nucleotide sequence of *Saccharomyces cerevisiae* chromosome XII"; NATURE, vol. 387; Issue No. 6632S Supplement to Nature; pp. 87–90 (May 29, 1997).

Kunst et al.; "The complete genome sequence of the Gram–positive bacterium *Bacillus subtilis*"; NATURE, vol. 390; pp. 249–256; Nov. 20, 1997.

Payne et al.; "Yeast Protein Database (YPD): a database for the complete proteome of *Saccharomyces cerevisiae*"; Nucleic Acids Research, vol. 25, No. 1; pp. 57–62 (Oct. 21, 1996).

Phillipsen et al.; "The nucleotide sequence of *Saccharomyces cerevisiae* chromosome XIV and its evolutionary implications"; NATURE vol. 387; Issue No. 6632S Supplement to Nature; pp. 93–98 (May 29, 1997).

Tettelin et al.; "The nucleotide sequence of *Saccharomyces cerevisiae* chromosome VII"; NATURE, vol. 387; Issue No. 6632S Supplement to Nature; pp. 81–84 (May 29, 1997).

*Primary Examiner*—Jennifer Graser
(74) *Attorney, Agent, or Firm*—Fish & Richardson P.C.

(57) ABSTRACT

Disclosed are genes found in *Streptococcus pneumoniae* that are essential for survival for a wide range of bacteria. These genes are termed "S-ylqF," "S-yqeG," "S-yybQ," "S-yerL," and "S-ysxC." These genes and the polypeptides that they encode, as well as homologs and orthologs thereof can be used to identify antibacterial agents for treating a broad spectrum of bacterial infections.

4 Claims, 18 Drawing Sheets

```
  1 ATGGCTACTATTCAATGGTTCCTGGTCACATGTCTAAAGCTCGTCAGAGTGCAGCAGTGCAGGAGAATTTAAATTGTTGATTTTGACGATTTAGTAGATG  100
    TACCGATGATAAGTTACCAAGGACCAGTGTACAGATTTCGAGCAGTCTCACGTCGTCCAGTCTCCTTAAATTTAAACAACTGCTAAATCATCTAC
  1 M  A  T  I  Q  W  F  P  G  H  M  S  K  A  R  R  Q  V  Q  E  N  L  K  F  V  D  F  V  T  I  L  V  D  A   34

101 CACGCTTGCCTCTATCTAGTCAAATCCTATGTTGACCAAGATTGTTGATAAACCAAAACTCTTGATTTTAAACAAGGCCGACTTGGCTGATCCAGC  200
    GTGCGAACGGAGATAGATCAGTTTAGGATACAACTGGTTCTAACAACCACTATTTGGTTTTGAGAACTAAAATTGTTCCGGCTGAACCGACTAGGTCG
 35 R  L  P  L  S  S  Q  N  P  M  L  T  K  I  V  G  D  K  P  K  L  L  I  L  N  K  A  D  L  A  D  P  A   67

201 AATGACCAAGGAATGGGCGTCAGTATTTGAATCACAAGGAATCCAAGAGCTATCAACTCCAAGAGCAAGTGACTGTAAAGTTGTAACAGATGCG  300
    TTACTGGTTCCTTACCGCAGTCATAAACTTAGTGTTCCTTAGGTCTGCGATCGATAGTTGAGGTTTCTCGTTCACTGACATTTCAACATGTCTACGC
 68 M  T  K  E  W  R  Q  Y  F  E  S  Q  G  I  Q  T  L  A  I  N  S  K  E  Q  V  T  V  K  V  V  T  D  A  100

301 GCCAAGAAGCTCATGGCTGATAAGATTGCTCGCCAGAAGAACGTGGGATTCAGATTGAAACCTTGGCTACTATGATTATCGGGATTCCAAACGCTGGTA  400
    CGGTTCTTCGAGTACCGACTATTCTAACGAGCGGTCTTCTTGCACCCTAAGTCTAACTTTGGAACGATGATACTAATAGCCCTAAGGTTTGCGACCAT
101 A  K  K  L  M  A  D  K  I  A  R  Q  K  E  R  G  I  Q  I  E  T  L  R  T  M  I  I  G  I  P  N  A  G  K  134

FIG. 1A
```

```
401 AATCAACTCTGATGAACCGTTTGGCTGTGGTGTTGGAAACAAGATTGCTGTCAAAAAGATTGCTGTAAAACAATGGCTTAAAACCAATAAGA 500
    TTAGTTGAGACTACTTGGCAAACCGACCATTTCTAACGACACAACCTTGTTCCGTTCCGTTCCAGTGTTTCCGAATTTGGTTATTCT

135  S  T  L  M  N  R  L  A  G  K  K  I  A  V  V  G  N  K  P  G  V  T  K  G  Q  Q  W  L  K  T  N  K  D  167

501 CCTGAAATCTTGGATACACCGGGGATTCTCTGGCCTAAGTTTGAGGATGAAACTGTTGCACTTAAGTTGGCATTGACTGGAGCTATCAAAGACCAGTTG 600
    GGACCTTTAGAGAACCTATGTGGCCCCTAAGAGACCGGATTCAAACTCCTACTTGACAACGTAACTGACCTCGATAGTTTCTGGTCAAC

168  L  E  I  L  D  T  P  G  I  L  W  P  K  F  E  D  E  T  V  A  L  K  L  A  L  T  G  A  I  K  D  Q  L  200

601 CTTCCTATGGATGAGGTTACCATTTTTGGTATCAATTATTCAAAGAACATTATCCAGAAAAGCTGGCTGAACGCTTCAAACAATGAAAATTGAAGAAG 700
    GAAGTTGAGACTACTCCAATGGTAAAAACCATAGTTAATAAGTTTCTGTAATAGGTCTTTCGACCGACTGCCGAAGTTGTTACTTTTAAGTCTTC

201  L  P  M  D  E  V  T  I  F  G  I  N  Y  F  K  E  H  Y  P  E  K  L  A  E  R  F  K  Q  M  K  I  E  E  E  234

701 AAGCGCCTGATTATTATGGATATGACCCGCGCCGCCCTCGGTTCCGTGATGACTATGACCGTTTTACAGTCTCTTCGTGAAGGAAGTCCGTGATGGCAA 800
    TTCGCGGACTAATAATACCTATACTGGGCGCGGCGGGAGCCAAGGCACTACTGATACTGGCAAAATGTCAGAGAAGCACTTCCTCAGGCACTACCGTT

235  A  P  V  I  I  M  D  M  T  R  A  L  G  F  R  D  D  Y  D  R  F  Y  S  L  F  V  K  E  V  R  D  G  K  267

801 ACTCCGGTAACTATACCTTAGATACATTGGAAGACCTCGATGCAACGATTAA  852    (SEQ ID NO: 1)
    TGAGCCATTGATATGGAATCTATGTAACCTTCTGGAGCTACGTTGCTAATT          (SEQ ID NO: 3)

268  L  G  N  Y  T  L  D  T  L  E  D  L  D  G  N  D  *  283         (SEQ ID NO: 2)
```

FIG. 1B

```
  1 ATGGCGATTGAAAATTATATACCGGATTTTGCTGTGGAAGCAGTCTATGATCTGACAGTCCCAAGCCTGCAGGGCGCAGGGAATAAAGGCTGTGTTTGGTCG 100
    TACCGCTAACTTTTAATATATGGCTAAACGACACCTTCGTCAGACTGTCAGAGTACTAGACAGTCTCGGACGTCGACGTCCCTATTTCCGACAAAACCAGC

1 M  A  I  E  N  Y  I  P  D  F  A  V  E  A  V  Y  D  L  T  V  P  S  L  Q  A  Q  G  I  K  A  V  L  V  D  34

101 ATTTGGATAATACCCTCATTGCTTGGAACAACCCTGATGGAACGCCAGAGATGAAGCAATGGCTACATGACCTTCGGAGACGGGTATTGGCATTATCGT 200
    TAAACCTATTATGGGAGTAACGAACGAACTTGTTGGGACTACCTTGCGGTCTCTACTTCGTTACCGATGTACTGGAAGCCTCTGCCCATAACCGTAATAGCA

35 L  D  N  T  L  I  A  W  N  N  P  D  G  T  P  E  M  K  Q  W  L  H  D  L  R  D  A  G  I  G  I  I  V  67

201 AGTGTCAAATAACACCAAAAAACGCGTTCAAGCGAGCAGTTGAACGATTACGTTTACTGGGCCTTGAGCCCTTCACATTGGTATTGAC 300
    TCACAGTTTATTGTGGTTTTTGCGCTTTTTGCGCAAGTTCGCTCGTCAACTTGCTACGAAATGCAAATGACCCGGAAGTGTAAACCATAACTG

```
301  CGTGCTATGAAGGAATTCCACTATGACAAAAAGGAAGTGGTCATGGTTGGTGACCAACTCATGACAGATATACGAGCAGCCACCGTGCAGGGATTCGGT    400
     GCACGATACTTCCTTAAGGTGATACTGTTTTTCCTTCACCAGTACCAACCACTGGTTGAGTACTGTCTATATGCTCGTCGGTGGCACGTCCCTAAGCCA
101  R  A  M  K  E  F  H  Y  D  K  K  E  V  V  M  V  G  D  Q  L  M  T  D  I  R  A  A  H  R  A  G  I  R  S        134

401  CAATTTTAGTCAAACCCTTGGTCCAACATGACTCAATCAAACGCAGATTAACCGAACTCGTGAGCGTCGTGTATGAGAAAATCACTGAAAAGTACGG    500
     GTTAAAATCAGTTTGGGAACCAGGTTGTACTGAGTTAGTTTGCGTCTAATTGGCTTGAGCACTCGCAGCACAATACTCTTTTAGTGACTTTTCATGCC
135  I  L  V  K  P  L  V  Q  H  D  S  I  K  T  Q  I  N  R  T  R  E  R  R  V  M  R  K  I  T  E  K  Y  G          167

501  ACCGATTACATATATAAAAGGAATTTAA  528    (SEQ ID NO: 4)
     TGGCTAATGTATATATTTTTCCTTAAATT         (SEQ ID NO: 6)
168  P  I  T  Y  K  K  G  I  *    175    (SEQ ID NO: 5)
```

FIG. 2B

```
  1 ATGTCCAAGATTCTAGTATTTGGTCACCAAAATCCAGACTCGAGATGCCATCGGTCATCGGTGTAGCTTTTGCCTACTTGGCAAAGAAGAGCTTACGGTTGG 100
    TACAGGTTCTAAGATCATAAAACCAGTGGTTTTAGGTCTGAGTCTACGGTAGACATCGAAAACGGATGAACGTTTCTTGAATGCCAAACC

1 M  S  K  I  L  V  F  G  H  Q  N  P  D  S  D  A  I  G  S  S  V  A  F  A  Y  L  A  K  E  A  Y  G  L  D  34

101 ATACGGAAGCTGTTGCCCTTGAACTCCAAATGAAGAAACAGCCTTGTCTTGAACTATTTGGTGTGAAGCACCAGTGTTATCACTTCTGCCAAAGC 200
    TATGCCTTCGACAACGGGAACCTTGAGTTTACTTCTTTGTCGGAAACGAACTTGATAAACACCACACTTGGTGTGCACAATAGTGAAGACGTTCG

35 I  E  A  V  A  L  G  T  P  N  E  E  T  A  F  V  L  N  Y  F  G  V  E  A  P  R  V  I  T  S  A  K  A  67

201 AGAGGGGGCAGAGCAAGTTATCTTGACTGACCACAATGAATTCCAACAATCTGTATCAGATATCGCTGAAGTAGAAGTTTACGGTGTTGTAGACCACCAC 300
    TCTCCCCCGTCTCGTTCAATAGAACTGACTGGTGTTACTTAAGGTTGTTAGACATAGTCTATAGCGACTTCATCTTCAAATGCCACACATCTGGTGGTG

68 E  G  A  E  Q  V  I  L  T  D  H  N  E  F  Q  Q  S  V  S  D  I  A  E  V  E  V  Y  G  V  V  D  H  H  100

301 CGTGTGGCTAACTTTGAAACTGCAAGCCCACTTTACATGCGTTTGGAGCCAGTTGGATCAGCTCTTCAATCGTTTACCGTATGTTCAAAGAACATGGTG 400
    GCACACCGATTGAAACTTTGACGTTCGGGTGAAATGTACGCAAACCTCGGTCAACTAGTCGAGAAGTTAGCAAATGGCATACAAGTTTCTTGTACCAC

```
401 TAGCTGTGCCTAAAGAGATTGCAGGTTTGATGCTTCAGTTTGATTTCAGATACCCTCTTTTGAAATCACCAACACACCCAACAGATAAAATCAT 500
    ATCGACACGGATTTCTAACGTCCAAACTACGAAGTCCAAACTAAAGTCTATGGGAAGAAAACTTTAGTGGTTGTGTGGGGTTGTCTATTTTAGTA

135  A  V  P  K  E  I  A  G  L  M  L  S  G  L  I  S  D  T  L  L  L  K  S  P  T  T  H  P  T  D  K  I  I   167

501 TGCTCCTGAATTGGCTGAATTGGCTGGTGTAAACTTGGAAGAATATGGTTTGGCAATGTTGAAAGCTGGTACCAACTTGGCTAGCAAATCGCTGAAGAA 600
    ACGAGGACTTAACCGACTTAACCGACCACATTTGAACCTTCTTATACCAAACGTTACAACTTCGACCATGGTTGAACCGATCGTTAGACGACTTCTT

168  A  P  E  L  A  E  L  A  G  V  N  L  E  E  Y  G  L  A  M  L  K  A  G  T  N  L  A  S  K  S  A  E  E   200

601 TTGATTGACATCGATGCTAAGACTTTTGAACTCAACGAGTTTGACATCGCTGAAGTTTGAACGCCAAG 700
    AACTAACTGTAGCTACGATTCTGAAACTTGAGTTGCCTTATTACAGGCACAACGGGTTCACTTGTGTCAACTGTAGCGACTTCAAACCTTGCGGTTC

701 CAGAAATTGAAGCTGCAATGCAAGCTGCCAACGAATCAAACGGCTACTCTGACTTTGTCTTGATGATTACAGATATCGTCAACTCAAACTCAGAAATATT 800
    GTCTTTAACTTCGACGTTACGTTCGACGGTTGCTTAGTTGCCGATGAGACTGAAACAGAACTACTAATGTCTATAGCAGTTGAGTTTGAGTCTTTATAA

235 E I E A A M Q A A N E S N G Y S D F V L M I T D I V N S N S E I L 267

801 GGCTCTTGGTGCCAATATGGACAAGGTCGAAGGGCTTTCATTTCAAACTTGAAAACATCATGCCTTCCTTGCTGGTGCCGTTCACGTAAGAAACAA 900
    CCGAGAACCACGGTTATACCGTTCCAGCTGTTCGCGAAAGTTAAAGTTTGAACTTTGTTAGTAGTACGGAAGGAACGACCACGGCAAAGTGCATTCTTGTT

268 A L G A N M D K V E A A F N F K L E N N H A F L A G A V S R K K Q 300

901 GTGGTACCTCAATTAACTGAAAGCTTTAATGCGTAA    936 (SEQ ID NO: 7)
    CACCATGGAGTTAATTGACTTTCGAAATTACGCATT        (SEQ ID NO: 9)

301 V V P Q L T E S F N A *    311 (SEQ ID NO: 8)

FIG. 3C

```
  1 ATGAAAATTACGCAAGAAGAGGTAACACACGTTGCCAATCTTTCAAAATTAAGATTCTGAAGAAGAAACTGCTGCCTTTGCCACCACCTTGTCTAAGA  100
    TACTTTTAATGCGTTCTTCCATTGTGTGCAACGGTTAGAACGTTTAATTCTAAGACTTCTCTTTGACGACGAAACGCTGGTGGAACAGATTCT

1 M  K  I  T  Q  E  E  V  T  H  V  A  N  L  S  K  L  R  F  S  E  E  E  T  A  A  F  A  T  T  L  S  K  I   34

101 TTGTTGACATGGTTGAATTGCTGGGCGAAGTTGACACAACTGGTGTCGCACCTACTACGGCGCCAGACTGTACTCCGCCCTGATGTGGC  200
    AACAACTGTACCAACTTAACGACCCGCTTCAACTGTGTTGACCACTGTGATGATGCCGCGGTCTGACATGAGGCGGGACTACACCG

35 V  D  M  V  E  L  L  G  E  V  D  T  T  G  V  A  P  T  T  T  M  A  D  R  K  T  V  L  R  P  D  V  A   67

201 CGAAGAAGGAATAGACCGTTGATCGCTTGTTTAAAAACGTACCTGAAAAAGACACTACTATATCAAGGTGCCAGTATCCTAGACAATGGAGGAGATGCC  300
    GCTTCTTCCTTATCTGGCACTAGCGAACAAATTTTGCATGGACTTTCTGTTGATGATATAGTTCCACGGTCATAGGATCTGTTACCTCCTACGG

68 E  E  G  I  D  R  D  R  L  F  K  N  V  P  E  K  D  N  Y  Y  I  K  V  P  A  I  L  D  N  G  G  D  A  100

301 TAA 303   (SEQ ID NO: 10)
    ATT       (SEQ ID NO: 12)

*      (SEQ ID NO: 11)
```

FIG. 4

```
   1  ATGGAACTTAATACACAATGCTGAAATCTGCTGCAGTGAGCTGCAGATGAACTGCCCTAGCAGGGCGTT  100
      TACCTTGAATTATGTGTTACGACTTTAGACGAGTGCACTCGACGTCCACTTGACGGTCTCTAACGGATGTCCCGCAA
   1   M  E  L  N  T  H  N  A  E  I  L  L  S  A  A  N  K  S  H  Y  P  Q  D  E  L  P  E  I  A  L  A  G  R  S   34

101  CAAATGTTGGTAAATCCAGCTTATCAACACTATGTGAAACCTGTAACCTAAGAATCTCGCCGTACATCAGGAAAACCTGTAAACCAGCTCGTGAACTTTT  200
      GTTTACAACCATTTAGGTCGAATAGTTGTGATACAACTTGGCATTCTTAGAGCGGGACATGTAGTCCTTTGGACCATTTGGGTCGAGGACTTGAAAAA
  35   N  V  G  K  S  S  F  I  N  T  M  L  N  R  K  N  L  A  R  T  S  G  K  P  G  K  T  Q  L  L  N  F  F     67

201  TAACATTGATGACAAGATGCGCTTTGTGGATGTGCCTGGTTATGCTGTATGCCTGGTTATGCTGTCTGTTTCTAAAAGAACGTGAAAAGTGGGGGTGCATGATTGAGGAG  300
      ATTGTAACTACTGTTCTACGCGAAACACTACACGATACGGATACGACCAATACGGATACCGATACGCAAAGATTTTCTTGCACTTTCCTCACCCCACGTACTAACTCCTC
  68   N  I  D  D  K  M  R  F  V  D  V  P  G  Y  G  Y  A  R  V  S  K  K  E  R  E  K  W  G  C  M  I  E  E   100

301  TACTTAACGACTCGGGAAAATCTCCGTGCGGTTCTCAGTCTAGTTGACCTTCGTCATGACCCTCAGCAGATGATGTCGAGATGTACGAATTTCTCAAGT  400
      ATGAATTGCTGAGCCCTTTTAGAGGCACGCCAACAGTCAGATCAACTGGAAGCACTGTCTACTACACGTCTACATGCTTAAAGAGTTCA
 101   Y  L  T  T  R  E  N  L  R  A  V  V  S  L  V  D  L  R  H  D  P  S  A  D  D  V  Q  M  Y  E  F  L  K  Y  134

401  ATTATGAGATTCCAGTCGTCATCATTGTCGCCAAGGCGGACAAGATTCCCGTGGTAAATGAACAAGCATGAATCAGCAATCAAAAGAAATTAAACTT  500
      TAATACTCTAAGGTCAGCAGTAGTAACACGGTTCCGCCGCTGTTGTCTAAGGAGCACCATTTACCTTGCTTACTACTTAGTCGTTAGTTTTCTTAATTGAA
 135   Y  E  I  P  V  I  I  V  A  T  K  A  D  K  I  P  R  G  K  W  N  K  H  E  S  A  I  K  K  K  L  N  F   167

501  TGACCCGAGTGACCGATTCATCTCTTTCATCTGTCAGTAAGGCAGGATGGATGAGGCTTGGGATGCAATCTTAGAAAAATTGTGA  588  (SEQ ID NO: 13)
      ACTGGGCTCACTGGCTAAGTAGAGAAGTAGACAGTCATTCCGTCCGTACCTACTCCGAACCCTACGTTAGAATCTTTTAACACT        (SEQ ID NO: 15)
 168   D  P  S  D  D  F  I  L  F  S  S  V  S  K  A  G  M  D  E  A  W  D  A  I  L  E  K  L  *             195  (SEQ ID NO: 14)

FIG. 5
```

```
  1 ATGACAATTCAATGGTTCCCGGGCCATATGGCAAAGCAAGGAAGTAACCGAAAAATTAAATTAATCGATATCGTATATGAATTGGTAGATGCCA  100
    TACTGTTAAGTTACCAAGGGCCCGGTATACCGTTTCGTTCCTTCATTGGCTCTTTTTAATTTAATTAGCTATAGCATATACTTAACATCTACGT
  1  M  T  I  Q  W  F  P  G  H  M  A  K  A  R  R  E  V  T  E  K  L  K  L  I  D  I  V  Y  E  L  V  D  A  R   34

101 GAATTCAATGTCATCATCAAGAACCAATGATGATTGAAGATATTCTAAAAAACAGCCGGAATTATGCTGTTAAACAGGCTGACAAAGCAGATGCGGCAGT  200
    CTTAAGTTACAGTAGTTCTTGGTTACTACTAACTTCTATAAGATTTTTGTTCGGCCTTAATACGACAATTGTTCGACTGTTCGTACGCGTCA
 35  I  P  M  S  S  R  N  P  M  I  E  D  I  L  K  N  K  P  R  I  M  L  L  N  K  A  D  K  A  D  A  A  V   67

201 TACACAGCAGTGGAAAGAGCACTTGAGAACCAGGAGATCCGCTCTCTGTCTATTAATTCTGTAAATGACAAGGGTTAAATCAATTGTGCCTGATCA  300
    ATGTGTCGTCACCTTCTCGTGAACTCTTGGTCCCCTAGGCGAGAGACAGATAATTAAGACATTACGTGTTCCCAATTAGTTAACAGGACGTAGT
 68  T  Q  Q  W  K  E  H  F  E  N  Q  G  I  R  S  L  S  I  N  S  V  N  G  Q  G  L  N  Q  I  V  P  A  S  100

301 AAAGAGATCCTCCAAGAAAATTTGACCGGATGCGGCTTGATTATCGGCATTCGCGGCTTTGATTATCGGCATCGCGGCTTGATTATCGGCGAAAAT  400
    TTTCTCTAGGAGGTTCTTTAAATGGCCTACGCCGAACTAACTAATAGCCGTAAGGTTGCAGCCTTTA
101  K  E  I  L  Q  E  K  F  D  R  M  R  A  K  G  V  K  P  R  A  I  R  A  L  I  I  G  I  P  N  V  G  K  S  134

401 CAACGCTCATCAACCGGCTTGCAAGAAAACATAGCAAAAACGGGAGACAGACCTGGTATTACGACTTCTCAACGTGGGTCAAGTTGGGAAGAATT  500
    GTTGCGAGTAGTTGGCCGAACGTTCTTTTGTATCGTTTTTGCCCCTCTGACCATAATGCTGAAGAGTTGTCACCCAGTTGTCAACCTTCTTAA
135  T  L  I  N  R  L  A  K  K  N  I  A  K  T  G  D  R  P  G  I  T  T  S  Q  Q  W  V  K  V  G  K  E  L  167
```

FIG. 6A

```
501 AGAGCTATTAGATACACCGGAATTTGTGGCCTAAATTTGAGGATGAGCTTGTCGGTTTGAGACTGGCAGTCACGGGCTATTAAAGACTCGATTATC 600
    TCTCGATAATCTATGTGGCCTTAAACACCGGATTTAAACTCCTACTCGAACAGCCAAACTCTGACCGTCAGTGCCCGATAATTTCTGAGCTAATAG

168 E  L  L  D  T  P  G  I  L  W  P  K  F  E  D  E  L  V  G  L  R  L  A  V  T  G  A  I  K  D  S  I  I 200

601 AATTTGCAGGACGTGGCCGTGTTTGGTCTTCGTTTCTCGAAGAACATTACCCAGAACGGCTTAAAGAGCGTTATGGCCTTGATGAGATCCCAGAGACA 700
    TTAAACGTCCTGCACCGGCACAAACCAGAAGCAAAGAGCTTCTTGTAATGGGTCTTGCCGAATTTCTGCAATACCGGAACTACTCTAGGGTCTCCTGT

201 N  L  Q  D  V  A  V  F  G  L  R  F  L  E  E  H  Y  P  E  R  L  K  E  R  Y  G  L  D  E  I  P  E  D 234

701 TTGCCGAGTCGTTGATGCAATAGGTGAAAAGCGGGGCTGTCTCATGAGCGGTGCTCATCAACTACGATAAGAGACTGAAGTCATCATTCGGATAT 800
    AACGGCTCAGCAACTACTAGTTATCCACTTTTCGCCCCGACAGAGTACTCGCCACGAGTAGTTGATGCTATTCTGCTGACTTCAGTAGTAAGGCTATA

235 A  E  L  F  D  A  I  G  E  K  R  G  C  L  M  S  G  G  L  I  N  Y  D  K  T  T  E  V  I  I  R  D  I 267

801 TCGCACTGAAAAGTTCGGCCAGGCTGTCATTTGAACAGCCGACGATG 846 (SEQ ID NO: 16)
    AGCGTGACTTTTCAAGCCGTCCGACAGTAAACTTGTCGGCTGCTAC      (SEQ ID NO: 18)

268 R  T  E  K  F  G  R  L  S  F  E  Q  P  T  M 282 (SEQ ID NO: 17)

FIG. 6B
```

```
  1 TTGTTAAAAAGTTTTTTTACCTGACGAGTTTGTAAAAATATTTTCATATTACACCTGAGAAATTAAAGGAACGAAATGTAAAGGAATTATTACTG 100
    AACAATTTTTCAAAAAAATGGACTGCTCAAACATTTTTATARAAAGTATAATGTGGACTCTTAATTCCTGCTCTTACATTTCCTTAATAATGAC
  1 L  L  K  K  F  F  L  P  D  E  F  V  K  N  I  F  H  I  T  P  E  K  L  K  E  R  N  V  K  G  I  L  T  D  34

101 ACCTGGATAATACGCTGTTGAATGGGACAGGCCGAACGGCGGATTGATGAGTGTTGAAGAAATGAAGGAACACGGCATTAAAGTGACAAT 200
    TGGACCTATTATGCGACAACTACCGTGTCCGGCTTGCGCTGCCGCCTAACTACTCTCACAACTTCTTACTTCCTGTGCCGTAATTTCACTGTTA
 35 L  D  N  T  L  V  E  W  D  R  P  N  A  T  P  R  L  I  E  W  F  E  E  M  K  E  H  G  I  K  V  T  I  67

201 TGTCTCTAATAATAACGAAAGAAGAGTGAAACTTTTCTCAGAACCGCTTGGAATCCATTCATCTATAAAGCAAGAAAACCGATGGGTAAGCCTTTAAT 300
    ACAGAGATTATTATTGCTTTCTTCTCACTTTGAAAAGAGTCTTGGCGAACCTTAGGTAAGTAGATATATTCGTTCTTTTGGCTACCCATTCGGAAATTA
 68 V  S  N  N  E  R  R  V  K  L  F  S  E  P  L  G  I  P  F  F  I  Y  K  A  R  K  P  M  G  K  A  F  N  100

301 AGAGCGGTCGCAATATGGAGCTGAAAAAGAGGACTGCGTTGTCATCGGAGACCAGCTGCTGACCGATGTACTCCGGGGAAACCGAAACGGCTACCATA 400
    TCTCGCCAGCGTTATACCTCGACTTTTTCTCCTGACGCAACAGTAGCCTCTGGTCGACGACTGGCTACATGAGCCCCTTTGGCTTTGCCGATGGTAT
101 R  A  V  R  N  M  E  L  K  K  E  D  C  V  V  I  G  D  Q  L  L  T  D  V  L  G  G  N  R  N  G  Y  H  T  134

401 CGATTTGGTGTGTGCCAGTCGCTTCCTCTGACGGATTCATTACGCCGCCTTAACCGCCAGTCGAACGCAGAATACTGAGTCGCTCAAACGAAAAGGCCA 500
    GCTAAACCAGCACGGTCAGCGAAGGAGACTGCCTAAGTAATGCGGCGGAATTGCGGGTCAGCTTGCGGTCCAGCTTATGACTCACGAGAGTTGCTTTCCGT
135 I  L  V  V  P  V  A  S  S  D  G  F  I  T  R  F  N  R  Q  V  E  R  R  I  L  S  A  L  K  R  K  G  H  167

501 CATTCAGTGGGAGGAG 516   (SEQ ID NO: 19)
    GTAAGTCACCCTCCTC       (SEQ ID NO: 21)
168 I  Q  W  E  E  172        (SEQ ID NO: 20)
```

FIG. 7

```
  1 ATGGAAAAGATACTTATTTTCGGACACCAAAACCCAGATACGATTGTCTGCATTGCTTATGCTGATTGAAAAACAAACTCGGCTTCATG 100
    TACCTTTTCTATGAATAAAAGCCTGTGGTTTGGGTCTATGTCTATGCTAAACAAGCGCTAAACGAATACGACTAAACTTTTGTTGAGCCGAAGTTAC
  1 M  E  K  I  L  I  F  G  H  Q  N  P  D  T  D  T  I  C  S  A  I  A  Y  A  D  L  K  N  K  L  G  F  N  A  34

101 CTGAGCCTGTCCGCTCGACAAGTCGTTCAGTGCCGTGTCAGTGCCGCTTGACTATTTCAAACAAGAAAGCCCGTCTCTGTGAAACAGCTGCAAACGA 200
    GACTCGGACAGGCGAGCGGAGCCTGTTCAGTGCCGTGTCAGTGCCGCTTGACTATTTGTATGCGAACTGATAAAGTTTGTTCTTCGGGCAGAACAACTTGTCGACGTTTGCT
 35 E  P  V  R  L  G  Q  V  N  G  E  T  Q  Y  A  L  D  Y  F  K  Q  E  S  P  R  L  V  E  T  A  A  N  E  67

201 AGTAAACGGCGTTATCCTGGTTGACATAACGCCAGCAAAGCATCAAAGACATTGAAGAGGTTCAGTTTTAGAGGTTATGCGACCATCACGCGATC 300
    TCATTTGCCCGCAATAGGACCAACTGTATTGCTGCGGTCGTCGTTCGTAGTTTCGTAACTTCTCCAAGTCCAATATCTCCAATAGCTGGTAGTGGCGTAG
 68 V  N  G  V  I  L  V  D  H  N  E  R  Q  Q  S  I  K  D  I  E  E  V  Q  V  L  E  V  I  D  H  H  R  I  100

301 GCTAACTTGAAACAGCTGAGCCGCTTACTATCGTGCTGAGCCTGTAGGCTGTAGGCTACCATCTTAAACAAAATGTACAAAGAGAATAACGTGAAAA 400
    CGATTGAAACTTTGTCGACTCGGCGAATGATAGCACGACTCGGACACATGCGATGTAGAATTGTTTACATGTTTCTTATTGCACTTT
101 A  N  F  E  T  A  E  P  L  Y  Y  R  A  E  P  V  G  C  T  A  T  I  L  N  K  M  Y  K  E  N  N  V  K  I  134

401 TCGAGAAAGAAATTGCCGGCCTTATGCTGTCTGCGATCATTTCTGATTCCCTGTTATTTAAATCTCCAACTTGCACGGACCAAGACGTAGCAGCAGCAAA 500
    AGCTCTTTCTTTAACGGCCGGAATACGACAGAGCGCTAGTAAGACTAAGGGACAATAAATTTAGAGGTTGAACGTGCCTGGTTCTGCATCGTCGTTT
135 E  K  E  I  A  G  L  M  L  S  A  I  I  S  D  S  L  L  F  K  S  P  T  C  T  D  Q  D  V  A  A  A  K  167
```

FIG. 8A

```
501 AGAGCTTGCGAGATCGCTGAGTGATAGATACGGCTTGAACATGTTGAAAGCAGGGCTGATCTAAGCAAAAACAGTGAAGAGCTCATT 600
    TCTCGAACGCTCTAGCGACTCATCTACGACTTCTATGCCGAACTTGTACAACTTCTGCCGGACTAGATTGTTTTTTGTCACTTCTCGAGTAA
168 E  L  A  E  I  A  G  V  D  A  E  E  Y  G  L  N  M  L  K  A  G  A  D  L  S  K  K  T  V  E  E  L  I  200

601 TCTCTTGATGCGAAGAATTACACTCGGCAGCAAGAAGTCGAAATCGCACAAGTGGACATTGAAGATGTAAAAAAACGCCAAGCTGAAT 700
    AGAGAACTACGCTTCTTAAATGTGAGCCGTCGTTCTTCAGCTTTAGCGTTCATTGTGTTCACCTGTAACTTCTACATTTTTTGCGGTTCGACTTA
201 S  L  D  A  K  E  F  T  L  G  S  K  K  V  E  I  A  Q  V  N  T  V  D  I  E  D  V  K  K  R  Q  A  E  L  234

701 TAGAAGCTGTGATCTCAAAGTTGTGGCTGAGAAGAATCTTGATCTGTTCCTTCTCGTTATCACAGATATCTTAGAAAATGATTCACTTGCTCTTGCAAT 800
    ATCTTCGACACTAGAGTTTCAACACCGACTCTTCTTAGAACTAGACAAGAAGAGCAATAGTGTCTATAGAATCTTTACTAAGTGAACGAGAACGTTA
235 E  A  V  I  S  K  V  V  A  E  K  N  L  D  L  F  L  L  V  I  T  D  I  L  E  N  D  S  L  A  L  A  I  267

801 CGGTAACGAAGCAGCGAAAGTGGAAAAGCGTTCAACGTTACATTAGAAAAACAACACAGCCCTCTAAAAGGCGTTGTTTCCCGTAAAAACAAGTCGTT 900
    GCCATTGCTTCGTCGCTTTCACCTTTTCGCAAGTTGCAATGTAATCTTTTGTTGTGTCGGGAGAATTTTCCGCAACAAAGGGCATTTTTGTTCAGCAA
268 G  N  E  A  A  K  V  E  K  A  F  N  V  T  L  E  N  N  T  A  L  L  K  G  V  V  S  R  K  K  Q  V  V  300

901 CCTGTCTTAACAGACGCAATGGCTGAA         927    (SEQ ID NO: 22)
    GGACAGAATTGTCTGCGTTACCGACTT                (SEQ ID NO: 24)
301 P  V  L  T  D  A  M  A  E           309    (SEQ ID NO: 23)
```

FIG. 8B

```
1    ATGTCACGAATTTCAATAGAAGAAGTAAAGCACGTTGCGCACCTTGCGATTACTGAAGAAGAAGCAAAATGTTCACTGAACAGCTCGACA    100
     TACAGTGCTTAAAGTTATCTTCTTCATTCGTGCAACGCGTGGAACGCTAATGACTTCTTCTTCGTTTTACAAGTGACTTGTCGAGCTGT

1     M  S  R  I  S  I  E  E  V  K  H  V  A  H  L  A  R  L  A  I  T  E  E  E  A  K  M  F  T  E  Q  L  D  S    34

101  GTATCATTTCATTTGCCGAGGAGCTTAATGAGGTTAACACAGACAATGTGGAGCCTACAACTCACGTGCTGAAATGTCATGAGAGAAGATGA    200
     CATAGTAAAGTAAACGGCTCCTCGAATTACTCCAATTGTGTCTGTTACACCTCGGATGTTGAGTGCACGACTTTACTTTACAGTACTCTTCTACT

35    I  I  S  F  A  E  E  L  N  E  V  N  T  D  N  V  E  P  T  T  H  V  L  K  M  K  N  V  M  R  E  D  E      67

201  AGCGGGTAAAGGTCTTCCGGTTGAGGATGTCATGAAAAATGCGCCTGACCATAAGAGACGGTATATTCGTGTGCCATCAATTCTGGAC    288 (SEQ ID NO: 25)
     TCGCCCATTTCCAGAAGGCCAACTCCTACAGTACTTTTACGCGGACTGGTATTTCTGCCGATATAAGCACACGGTAGTTAAGACCTG         (SEQ ID NO: 27)

68    A  G  K  G  L  P  V  E  D  V  M  K  N  A  P  D  H  K  D  G  Y  I  R  V  P  S  I  L  D         96 (SEQ ID NO: 26)
```

FIG. 9

```
  1 ATGAAGTCACAAGTCAGAAATCGTGATCAGTGCAGTAAAACCGGAACAGTCCCTGAAGGGGGCTTCCCGAAATGCCGAAATCGAACG   100
    TACTTCAGTGTTCAGTCTTTAGCAGTCACTAGTCACTGTCATGGGACTTCCCCGAAGCCTTTAGCGTAACGGCCTTCTAGCTGC       34
  1 M  K  V  T  K  S  E  I  V  I  S  A  V  K  P  E  Q  Y  P  E  G  G  L  P  E  I  A  L  A  G  R  S  N  V

101 TAGGAAAATCGTCTTTATCAATTCATAATCAATCAGTAGTAATTAGCGTTTAGAACGCTCTTGCAGTAGTTGCAGAAGCTCATCAAAGCCGGGAAAACAAGCTTAATTCTACATTAT   200
    ATCCTTTTAGCAGAAATAGTAGTAATTAGTAGGCTTTAGAAGCGTTTAGAACGCTCTTGCAGTAGTTGCACAGTTCGGCCCCTTTGTGTTCGAAATTAAGATGTAATA          67
 35 G  K  S  S  F  I  N  S  L  I  N  R  K  H  L  A  R  T  S  S  K  P  G  K  T  Q  T  L  N  F  Y  I  I

201 CAATGATGAGCTGCATTTGTGGATGTCCAGATCGTTGATTTGGGCATGCCATCTAATGATGCAGATGTACAGATGTATGAATTTTAAGTATTACG   300
    GTTACTACTCGACGTAAACACCTACAGGTTCAGCAACTGATAGACAACTAAACCCCCGTACCCGGGTCGCACTCGTACACTTCACTTGGATATAG             100
 68 N  D  E  L  H  F  V  D  V  P  G  Y  G  F  A  K  V  S  K  S  E  R  E  A  W  G  R  M  I  E  T  Y  I

301 ACGACACGGGAGAATTAAAGCTGTGCAGATCGTTGTGCAGATCTTGATTTGGGCATGCCATCTAATGATGCACAGATGTACAGATGTATGAATTTTAAGTATTACG   400
    TGCTGTGCCTCCTTAAATTTTCGACACGTCTAGTTCAGAACTAAAGCCGTACGGGTCGCACTCGTACACTTCACTTGGATATAG                         134
101 T  T  R  E  E  L  K  A  V  V  Q  I  V  D  L  R  H  A  P  S  N  D  D  V  Q  M  Y  E  F  L  K  Y  Y  G

401 GCATTCCTGTTATTGTATCGCTACAAAGGGCGGATAAGATCCCGAAAGGTAAATGGGACAAACACGGCAAGGTTGTCCGACAAACATTAAATATTGATCC   500
    CGTAAGGACAATAACCATAGCGATGTTTCCGCCTATTCTAGGGCTTTCCATTTACCCTGTTTGTGCCGTTCCAACAGGCTGTTGTAATTATAACTAGG            167
135 I  P  V  I  V  I  A  T  K  A  D  K  I  P  K  G  K  W  D  K  H  A  K  V  V  R  Q  T  L  N  I  D  P

501 GGAAGACGAGCTGATCCTCTTTTCTTCAGAAACGAAAAGAAGCGAAGCTTGGGAGAGCGAAGATGAAGCGGATCAAAAAATGATAAACCGG   585 (SEQ ID NO: 28)
    CCTTCTGCTCGACTAGGAGAAAAGAAGAGTCTTTGCTTTCCCTTTCGCTTCGACTTCGAACCCCTCGCTAGTTTTTTACTATTTGGCC          (SEQ ID NO: 30)
168 E  D  E  L  I  L  F  S  S  E  T  K  K  G  K  D  E  A  W  G  A  I  K  K  M  I  N  R                195 (SEQ ID NO: 29)
```

FIG. 10

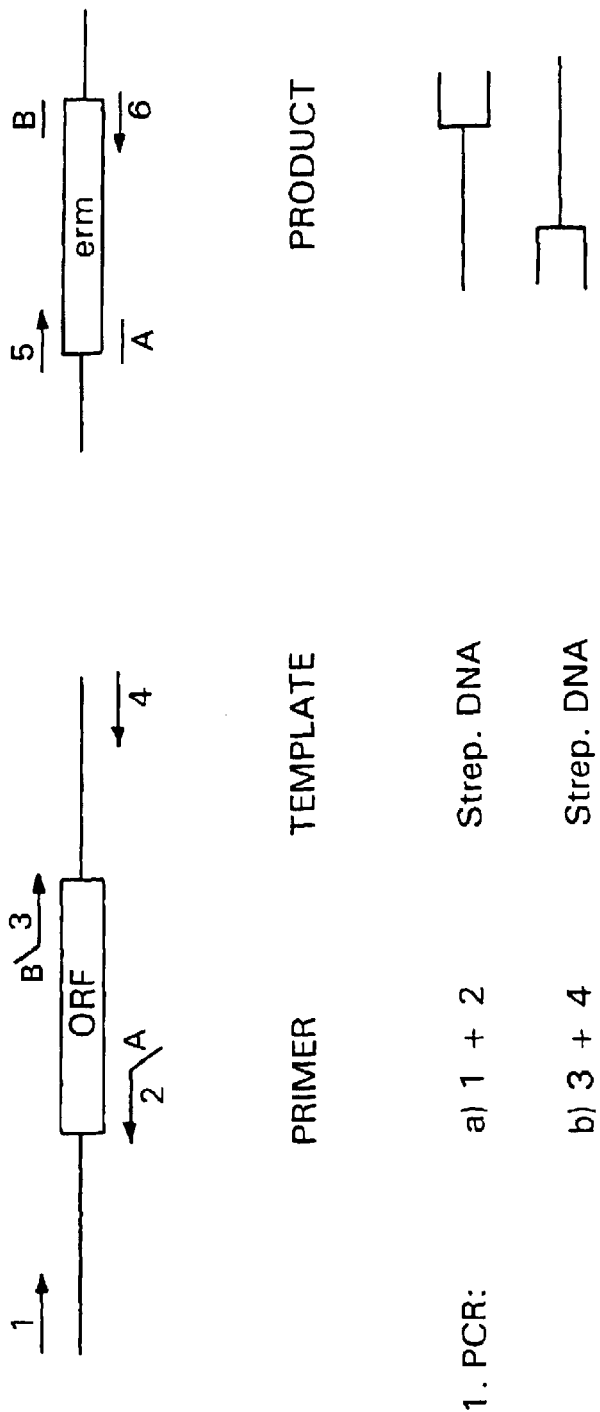

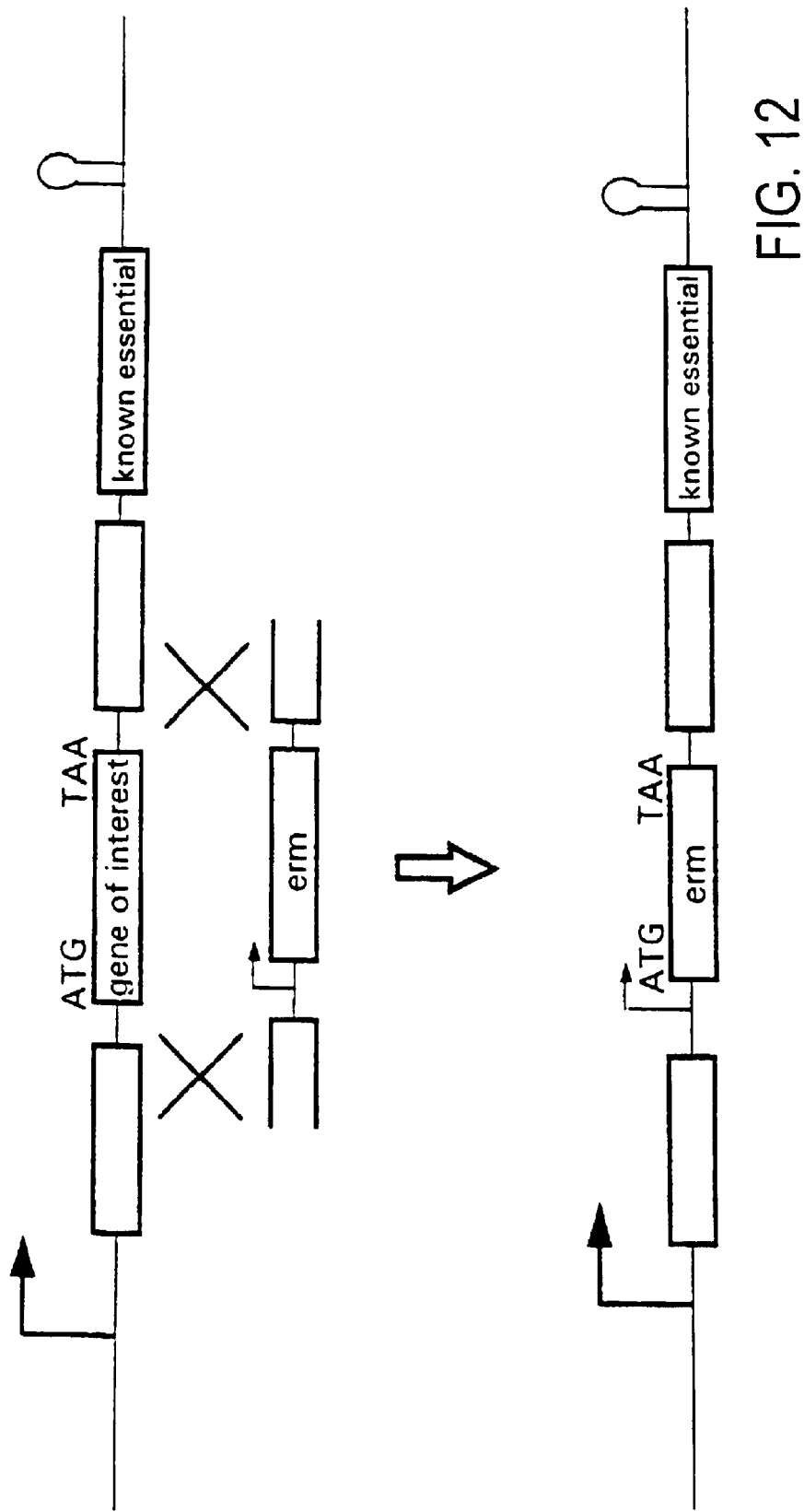

ically pathogenic to humans are gram positive bacteria. The bac-
USE OF YLQF, YQEG, YYBQ, AND YSXC, ESSENTIAL BACTERIAL GENES AND POLYPEPTIDES

RELATED APPLICATION INFORMATION

This application is a divisional of application Ser. No. 10/023,528, filed on Dec. 17, 2001 (now U.S. Pat. No. 6,638,729), which is a divisional of application Ser. No. 09/222,939, filed on Dec. 30, 1998 (now U.S. Pat. No. 6,372,448). The contents of both of these applications is incorporated herein by reference in its entirety.

FIELD OF THE INVENTION

The invention relates to the use of ylqF, yqeG, yybQ, yerL, and ysxC, essential bacterial genes and polypeptides in identifying antibacterial agents.

BACKGROUND OF THE INVENTION

Bacterial infections may be cutaneous, subcutaneous, or systemic. Opportunistic bacterial infections proliferate, especially in patients afflicted with AIDS or other diseases that compromise the immune system. Most bacteria that are pathogenic to humans are gram positive bacteria. The bacterium Streptococcus pneumoniae, for example, typically infects the respiratory tract and can cause lobar pneumonia, as well as meningitis, sinusitis, and other infections.

SUMMARY OF THE INVENTION

The invention is based on the identification of ten genes of the gram positive bacterium Streptococcus pneumoniae and of Bacillus subtilis as being essential for survival. The Streptococcus pneumoniae genes are termed "S-ylqF," "S-yqeG," "S-yybQ," "S-yerL," and "S-ysxC." The orthologs of these genes in Bacillus subtilis are termed "B-ylqF," "B-yqeG," "B-ybQ," "B-yerL," and "B-ysxC," respectively. The terms "ylqF," "yqeG," "yybQ," "yerL," and "ysxC" genes and polypeptides are used to refer to the Streptococcus pneumoniae and Bacillus subtilis genes and polypeptides, as well as their homologs and orthologs, collectively. While "homologs" are structurally similar genes contained within a species, "orthologs" are functionally equivalent genes from other species (within or outside of a given genus, e.g., from E. coli). These genes are considered "essential" genes, and their polypeptides are considered "essential" polypeptides. Each gene and polypeptide can be used in methods for identifying similar genes and polypeptides in pathogenic and non-pathogenic microorganisms. Each polypeptide can be used to identify compounds that are inhibitors of the pathogens in which the polypeptide (ylqF, yqeG, yybQ, yerL, or ysxC) is expressed. Such inhibitors attenuate bacterial growth by inhibiting the activity of ylqF, yqeG, yybQ, yerL, or ysxC polypeptide, or by inhibiting gene transcription or translation.

The amino acid and nucleic acid sequences of the essential polypeptides described herein are set forth in FIGS. 1–10 as shown in Table 1.

TABLE 1

Essential Polypeptides Disclosed Herein

| Essential Nucleic Acid or Polypeptide | FIG. NO. | SEQ ID NO. of Amino Acid Sequence | SEQ ID NO. of the Coding Strand of the Nucleic Acid Sequence | SEQ ID NO. of the Non-coding Strand of the Nucleic Acid Sequence |
|---|---|---|---|---|
| S-ylqF | 1A-1B | 2 | 1 | 3 |
| S-yqeG | 2A-2B | 5 | 4 | 6 |
| S-yybQ | 3A-3C | 8 | 7 | 9 |
| S-yerL | 4 | 11 | 10 | 12 |
| S-ysxC | 5 | 14 | 13 | 15 |
| B-ylqF | 6A-B | 17 | 16 | 18 |
| B-yqeG | 7 | 20 | 19 | 21 |
| B-yybQ | 8A-8B | 23 | 22 | 24 |
| B-yerL | 9 | 26 | 25 | 27 |
| B-ysxC | 10 | 29 | 28 | 30 |

Since these genes have been identified and shown to be essential for survival, these genes and polypeptides (including homologs and orthologs of the sequences disclosed herein) can be used to identify antibacterial agents. Such antibacterial agents can readily be identified with high throughput assays to detect inhibition of the metabolic pathway in which these essential polypeptides participate. This inhibition can be caused by small molecules interacting with (e.g., binding directly or indirectly to) the ylqF polypeptide, for example, or other essential polypeptides in that pathway.

In an exemplary assay, but not the only assay, a promoter that responds to depletion of the ylqF, yqeG, yybQ, yerL, or ysxC polypeptide by upregulation or downregulation is linked to a reporter gene. To identify a promoter that is up- or down-regulated by the depletion of the polypeptide, the gene encoding the polypeptide is deleted from the genome and replaced with a version of the gene in which the sequence encoding the polypeptide (ylqF, yqeG, yybQ, yerL, or ysxC) is operably linked to a regulatable promoter. The cells containing this regulatable genetic construct are kept alive by the essential polypeptide produced from the genetic construct containing the regulatable promoter. However, the regulatable promoter allows the expression of the polypeptide to be reduced to a level that causes growth inhibition. Total RNA prepared from bacteria under such growth-limiting conditions is compared with RNA from wild-type cells. Standard methods of transcriptional profiling can be used to identify mRNA species that are either more or less abundant (i.e., up- or down-regulated) when expressed under the limiting conditions. Genomic sequence information, e.g., from GenBank, can be used to identify a promoter that drives expression of the identified RNA species. Such promoters are up- or down-regulated by depletion of the ylqF, yqeG, yybQ, yerL, or ysxC polypeptide.

Having identified a promoter(s) that is up- or down-regulated by depletion of the essential polypeptide (ylqF, yqeG, yybQ, yerL, or ysxC), the promoter(s) is operably linked to a reporter gene (e.g., β-galactosidase, gus, or green fluorescent protein (GFP)). A bacterial strain containing this reporter gene construct is then exposed to test compounds. Compounds that inhibit the ylqF, yqeG, yybQ, yerL, or ysxC polypeptide (or other polypeptides in the essential pathway in which the polypeptide participates) will cause a functional depletion of the polypeptide and therefore lead to an upregulation or downregulation of expression of the reporter gene. Because the polypeptides described herein are essential for the survival of bacteria, compounds that inhibit these polypeptides in such an assay are expected to be antibacterial and can be further tested, if desired, in standard susceptibility assays.

Another suitable method for identifying antibacterial compounds involves screening for small molecules that specifically interact with (i.e., bind directly or indirectly to) the ylqF, yqeG, yybQ, yerL, or ysxC polypeptide. A variety of suitable interaction and binding assays are known in the art as described, for example, in U.S. Pat. Nos. 5,585,277 and 5,679,582, incorporated herein by reference. For example, in various conventional assays, test compounds can be assayed for their ability to interact with a ylqF polypeptide by measuring the ability of the small molecule to stabilize the ylqF polypeptide in its folded, rather than unfolded, state. More specifically, one can measure the degree of protection against unfolding that is afforded by the test compound. Test compounds that bind, for example, the ylqF polypeptide with high affinity cause, for example, a large shift in the temperature at which the polypeptide is denatured. Test compounds that stabilize the ylqF polypeptide in a folded state can be further tested for antibacterial activity in a standard susceptibility assay. Similar assays can be performed with the other essential polypeptides described herein.

In a related method for identifying antibacterial compounds, the ylqF, yqeG, yybQ, yerL, or ysxC polypeptide is used to isolate peptide or nucleic acid ligands that specifically bind the polypeptide. These peptide or nucleic acid ligands are then used in a displacement screen to identify small molecules that interact with the polypeptide. Such assays can be carried out essentially as described above.

Another suitable method for identifying inhibitors of the ylqF, yqeG, yybQ, yerL, or ysxC polypeptides involves identifying a biochemical activity of the polypeptide and then screening for small molecule inhibitors of the activity using, for example, a high throughput screening method.

The ylqF, yqeG, yybQ, yerL, and ysxC polypeptides can be used, separately or together, in assays to identify test compounds that interact with these polypeptides. Test compounds that interact with these polypeptides then can readily be tested, in conventional assays, for their ability to inhibit bacterial growth. Test compounds that interact with the ylqF, yqeG, yybQ, yerL, or ysxC polypeptides are candidate antibacterial agents, in contrast to compounds that do not interact with the ylqF, yqeG, yybQ, yerL, or ysxC polypeptides. As described herein, any of a variety of art-known methods can be used to assay for the interaction of test compounds with the ylqF, yqeG, yybQ, yerL, or ysxC polypeptides.

The invention also includes a method for identifying an antibacterial agent where the method entails: (a) contacting a ylqF, yqeG, yybQ, yerL, or ysxC polypeptide with a test compound; (b) detecting binding of the test compound to the polypeptide; and, optionally, (c) determining whether a test compound that binds to the polypeptide inhibits growth of bacteria, relative to growth of bacteria cultured in the absence of the test compound that binds to the polypeptide, as an indication that the test compound is an antibacterial agent.

In still another method, interaction of a test compound with a ylqF, yqeG, yybQ, yerL, or ysxC polypeptide (e.g., binding) can be detected in a conventional two-hybrid system for detecting protein/protein interactions (e.g., in yeast or mammalian cells). A test polypeptide found to interact with the ylqF, yqeG, yybQ, yerL, or ysxC polypeptide can be further tested for antibacterial activity in a conventional susceptibility assay. Generally, in such two-hybrid methods, (a) the ylqF, yqeG, yybQ, yerL, or ysxC polypeptide is provided as a fusion protein that includes the essential polypeptide fused to (i) a transcription activation domain of a transcription factor or (ii) a DNA-binding domain of a transcription factor; (b) the test compound is provided as a fusion protein that includes a test polypeptide fused to (i) a transcription activation domain of a transcription factor or (ii) a DNA-binding domain of a transcription factor; and (c) binding of the test polypeptide to the ylqF, yqeG, yybQ, yerL, or ysxC polypeptide is detected as a reconstitution of a transcription factor. Homologs and orthologs of the polypeptides described herein can be used in such methods. Reconstitution of the transcription factor can be detected, for example, by detecting transcription of a gene that is operably linked to a DNA sequence bound by the DNA-binding domain of the reconstituted transcription factor (See, for example, White, 1996, Proc. Natl. Acad. Sci. 93:10001–10003 and references cited therein and Vidal et al., 1996, Proc. Natl. Acad. Sci. 93:10315–10320).

In an alternative method, an isolated nucleic acid molecule encoding ylqF, yqeG, yybQ, yerL, or ysxC is used to identify a compound that decreases the expression of the polypeptide in vivo (i.e., in a cell). Such compounds can be used as antibacterial agents. To discover such compounds, cells that express a ylqF, yqeG, yybQ, yerL, or ysxC polypeptide are cultured, exposed to a test compound (or a mixture of test compounds), and the level of ylqF, yqeG, yybQ, yerL, and ysxC expression or activity is compared with the level of expression or activity in cells that are otherwise identical but that have not been exposed to the test compound(s). Many standard quantitative assays of gene expression can be utilized in this aspect of the invention.

To identify compounds that modulate expression of a ylqF, yqeG, yybQ, yerL, or ysxC polypeptide, the test compound(s) can be added at varying concentrations to the culture medium of cells that express the polypeptide, as described herein. Such test compounds can include small molecules (typically, non-protein, non-polysaccharide chemical entities), polypeptides, and nucleic acids. The expression of the polypeptide is then measured, for example, by Northern blot PCR analysis or RNAse protection analyses using a nucleic acid molecule described herein as a probe. The level of expression in the presence of the test molecule, compared with the level of expression in its absence, will indicate whether or not the test molecule alters the expression of the polypeptide. Because the ylqF, yqeG, yybQ, yerL, and ysxC polypeptides (including homologs and orthologs of the sequences disclosed herein) are essential for survival, test compounds that inhibit the expression and/or function of any of these polypeptides will inhibit growth of, or kill, the cells that express such polypeptides.

Typically, the test compound will be a small organic molecule. Alternatively, the test compound can be a test polypeptide (e.g., a polypeptide having a random or predetermined amino acid sequence; or a naturally-occurring or synthetic polypeptide) or a nucleic acid, such as a DNA or RNA molecule. The test compound can be a naturally-occurring compound or it can be synthetically produced, if desired. Synthetic libraries, chemical libraries, and the like can be screened to identify compounds that bind the ylqF, yqeG, yybQ, yerL, or ysxC polypeptide. More generally, binding of test a compound to the polypeptide can be detected either in vitro or in vivo. If desired, the above-described methods for identifying compounds that modulate the expression of the essential-polypeptides of the invention can be combined with measuring the levels of the essential polypeptides of the invention expressed in the cells, e.g., by performing a Western blot analysis using antibodies that bind one of the polypeptides.

Regardless of the source of the test compound, the essential polypeptides of the invention can be used to identify compounds that inhibit the activity of a ylqF, yqeG, yybQ, yerL, or ysxC polypeptide, or inhibit transcription of a gene encoding such a polypeptide, or inhibit translation of the mRNA transcribed from such a gene. These antibacterial agents can be used to inhibit a wide spectrum of pathogenic- or non-pathogenic bacterial strains, particularly gram-positive bacteria.

In other embodiments, the invention includes pharmaceutical formulations that include a pharmaceutically acceptable excipient and an antibacterial agent identified using the methods described herein. In particular, the invention includes pharmaceutical formulations that contain antibacterial agents that inhibit the growth of, or kill, pathogenic bacterial strains (e.g., pathogenic gram positive bacterial strains such as pathogenic Streptococcus strains). Such pharmaceutical formulations can be used in a method of treating a bacterial infection in an organism (e.g., a Streptococcus infection). Such a method entails administering to the organism a therapeutically effective amount of the pharmaceutical formulation, i.e., an amount sufficient to ameliorate signs and/or symptoms of the bacterial infection. In particular, such pharmaceutical formulations can be used to treat bacterial infections in mammals such as humans and domesticated mammals (e.g., cows, pigs, dogs, and cats), and in plants. The efficacy of such antibacterial agents in humans can be estimated in an animal model system well known to those of skill in the art (e.g., mouse and rabbit model systems of, for example, streptococcal pneumonia).

Various affinity reagents that are permeable to the microbial membrane (i.e., antibodies and antibody fragments) are useful in practicing the methods of the invention. For example polyclonal and monoclonal antibodies that specifically bind to a ylqF, yqeG, yybQ, yerL, or ysxC polypeptide can facilitate detection of such polypeptides in various bacterial strains (or extracts thereof). These antibodies also are useful for detecting binding of a test compound to such polypeptides (e.g., using the assays described herein). In addition, monoclonal antibodies that bind these essential polypeptides can themselves be used as antibacterial agents.

The invention further features methods of identifying from a large group of mutant strains those strains that have conditional lethal mutations. In general, the gene and corresponding gene product are subsequently identified, although the strains themselves can be used in screening or diagnostic assays. The mechanism(s) of action for the identified genes and gene products provide a rational basis for the design of antibacterial therapeutic agents. These antibacterial agents reduce the action of the gene product in a wild type strain, and therefore are useful in treating a subject with that type, or a similarly susceptible type, of infection by administering the agent to the subject in a pharmaceutically effective amount. Reduction in the action of the gene product includes competitive inhibition of the gene product for the active site of an enzyme or receptor; non-competitive inhibition; disrupting an intracellular cascade path which requires the gene product; binding to the gene product itself, before or after post-translational processing; and acting as a gene product mimetic, thereby down-regulating the activity. Therapeutic agents include monoclonal antibodies raised against the gene product.

Furthermore, the presence of the gene sequence in certain cells (e.g., a pathogenic bacterium of the same genus or similar species), and the absence or divergence of the sequence in host cells can be determined, if desired. Therapeutic agents directed toward genes or gene products that are not present in the host have several advantages, including fewer side effects, and lower overall dosage.

In various embodiments, the ylqF, yqeG, yybQ, yerL, and ysxC polypeptides used in the assays described herein are derived from a non-pathogenic or pathogenic gram positive bacterium. For example, these polypeptides can be derived from a Streptococcus strain, such as *Streptococcus pneumoniae, Streptococcus pyogenes, Streptococcus agalactiae, Streptococcus endocarditis, Streptococcus faecium, Streptococcus sangus, Streptococcus viridans*, and *Streptococcus hemolyticus*. Suitable orthologs of the S-ylqF, S-yqeG, S-yybQ, S-yerL, and S-ysxC genes can be derived from a wide spectrum of bacteria, such as *Bacillus subtilis* and *E. coli*. The *Bacillus subtilis* orthologs are B-ylqF, B-yqeG, B-yybQ, B-yerL, B- and B-ysxC, respectively.

The invention offers several advantages. For example, the methods for identifying antibacterial agents can be configured for high throughput screening of numerous candidate antibacterial agents. Because the essential genes disclosed herein are thought to be highly conserved, antibacterial drugs targeted to these genes or their gene products are expected to have a broad spectrum of antibacterial activity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated herein by reference in their entirety. In the case of a conflict, the present specification, including definitions, will control. In addition, the materials, methods, and examples are illustrative and are not intended to limit the scope of the invention, which is defined by the claims.

Other features and advantages of the invention will be apparent from the following detailed description, and from the claims.

BRIEF DESCRIPTION OF THE DRAWINGS

FIGS. 1A–1B is a listing of the amino acid and coding strand and non-coding strand nucleic acid sequences of a S-ylqF polypeptide and gene from a *Streptococcus pneumoniae* strain (SEQ ID NOs:2, 1, and 3, respectively).

FIGS. 2A–2B is a listing of the amino acid and coding strand and non-coding strand nucleic acid sequences of a S-yqeG polypeptide and gene from a *Streptococcus pneumoniae* strain (SEQ ID NOs:5, 4, and 6, respectively).

FIGS. 3A–3C is a listing of the amino acid and coding strand and non-coding strand nucleic acid sequences of a S-yybQ polypeptide and gene from a *Streptococcus pneumoniae* strain (SEQ ID NOs:8, 7 and 9, respectively).

FIG. 4 is a listing of the amino acid and coding strand and non-coding strand nucleic acid sequences of a S-yerL polypeptide and gene from a *Streptococcus pneumoniae* strain (SEQ ID NOs:11, 10, and 12, respectively).

FIG. 5 is a listing of the amino acid and coding strand and non-coding strand nucleic acid sequences of a S-ysxC polypeptide and gene from a *Streptococcus pneumoniae* strain (SEQ ID NOs:14, 13, and 15, respectively).

FIGS. 6A–6B is a listing of the amino acid and coding strand and non-coding strand nucleic acid sequences of a B-ylqF polypeptide and gene from a *Streptococcus pneumoniae* strain (SEQ ID NOs:17, 16, and 18, respectively).

FIG. 7 is a listing of the amino acid and coding strand and non-coding strand nucleic acid sequences of a B-yqeG polypeptide and gene from a *Streptococcus pneumoniae* strain (SEQ ID NOs:20, 19, and 21, respectively).

FIGS. 8A–8B is a listing of the amino acid and coding strand and non-coding strand nucleic acid sequences of a B-yybQ polypeptide and gene from a *Streptococcus pneumoniae* strain (SEQ ID NOs:23, 22, and 24, respectively).

FIG. 9 is a listing of the amino acid and coding strand and non-coding strand nucleic acid sequences of a B-yerL polypeptide and gene from a *Streptococcus pneumoniae* strain (SEQ ID NOs:26, 25, and 27, respectively).

FIG. 10 is a listing of the amino acid and coding strand and non-coding strand nucleic acid sequences of a B-ysxC polypeptide and gene from a *Streptococcus pneumoniae* strain (SEQ ID NOs:29, 28, and 30, respectively).

FIG. 11 is a schematic representation of the PCR strategy used to produce DNA molecules used for targeted deletions of essential genes in *Streptococcus pneumoniae*.

FIG. 12 is a schematic representation of the strategy used to produce targeted deletions of essential genes in *Streptococcus pneumoniae*.

DETAILED DESCRIPTION OF THE INVENTION

Various genes in the bacterium *Streptococcus pneumoniae* have each been found to be essential for the survival of this bacterium. These essential genes have been termed S-ylqF, S-yqeG, S-yybQ, S-yerL, and S-ysxC. These genes can be used to identify homologs and orthologs in pathogenic microorganisms, such as pathogenic gram-positive bacteria (e.g., Bacillus). The *Bacillus subtilis* orthologs of these essential *Streptococcus pneumoniae* genes have been termed B-ylqF, B-yqeG, B-yybQ, B-yerL, and B-ysxC and are essential for survival. The essential polypeptides described herein can be used in methods for identifying compounds that are inhibitors of the pathogens in which these polypeptides are expressed (e.g., pathogenic and non-pathogenic bacteria, and gram-positive bacteria in particular).

Nucleic acids used in practicing the methods of the invention include both RNA and DNA, including genomic DNA and synthetic (e.g., chemically synthesized) DNA. Nucleic acids can be double-stranded or single-stranded. Where single-stranded, the nucleic acid may be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An isolated nucleic acid is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence. The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an isolated nucleic acid fragment is a nucleic acid fragment that is not naturally occurring as a fragment and would not be found in the natural state.

A nucleic acid sequence that is substantially identical to an S-ylqF or B-ylqF nucleotide sequence is at least 80% identical to the nucleotide sequence represented by SEQ ID NO:1, as depicted in FIGS. 1A–1B. Likewise, nucleic acid sequences that are substantially identical to each of the other essential genes disclosed herein are at least 80% identical to each of the nucleotide sequences presented by SEQ ID NOs:1, 4, 7, 10, 13, 18, 21, 22, 25, and 30, as depicted in FIGS. 2A–10, respectively. For purposes of comparison of nucleic acids, the length of the reference nucleic acid sequence will generally be at least 40 nucleotides, e.g., at least 60 nucleotides or more nucleotides.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, the molecules are identical at that position. The percent identity between the two sequences is a function of the number of identical positions shared by the sequences (i.e., % identity=# of identical positions/total # of overlapping positions×100). Preferably, the two sequences are the same length.

The determination of percent identity or homology between two sequences can be accomplished using a mathematical algorithm. A suitable, mathematical algorithm utilized for the comparison of two sequences is the algorithm of Karlin and Altschul (1990) *Proc. Nat'l Acad. Sci. USA* 87:2264–2268, modified as in Karlin and Altschul (1993) *Proc. Nat'l Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to yneS protein molecules. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. See http://www.ncbi.nlm.nih.gov. Another example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The essential polypeptides useful in practicing the invention include, but are not limited to, recombinant polypeptides and natural polypeptides. Also useful in the invention are nucleic acid sequences that encode forms of the ylqF, yqeG, yybQ, yerL, or ysxC polypeptides in which naturally occurring amino acid sequences are altered or deleted. Preferred nucleic acids encode polypeptides that are soluble under normal physiological conditions. Also useful are nucleic acids encoding fusion proteins in which a portion of one of the essential polypeptides described herein is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells. Also useful in practicing the methods of the invention are isolated polypeptides (and the nucleic acids that encode these polypeptides) that include a first portion and a second portion; the first portion includes, e.g., a ylqF polypeptide, and the second portion includes an immunoglobulin constant (Fc) region or a detectable marker.

The fusion partner can be, for example, a polypeptide which facilitates secretion, e.g., a secretory sequence. Such a fused polypeptide is typically referred to as a preprotein. The secretory sequence can be cleaved by the host cell to form the mature protein. Additional useful nucleic acids include nucleic acids that encode, for example, a ylqF polypeptide fused to a polypeptide sequence to produce an inactive preprotein. Preproteins can be converted into the active form of the protein by removal of the inactivating sequence.

Nucleic acids that hybridize, e.g., under stringent or highly stringent hybridization conditions (as defined herein) to all or a portion of a nucleotide sequence represented by SEQ ID NOs:1, 4, 7, 10, 13, 18, 21, 22, 25, or 30, or their complements, can be used to identify additional homologs or orthologs of the essential genes described herein. The hybridizing portion of the hybridizing nucleic acids is typically at least 15 (e.g., 20, 25, 30, or 50) nucleotides in length. The hybridizing portion of the hybridizing nucleic acid is at least 80%, e.g., at least 95%, or at least 98%, identical to the sequence of a portion or all of a nucleic acid encoding one of the essential polypeptides described herein or its complement. Hybridizing nucleic acids of the type described herein can be used as a cloning probe, a primer (e.g., a PCR primer), or a diagnostic probe. Nucleic acids that hybridize to the nucleotide sequences represented by SEQ ID NOs:1, 4, 7, 10, 13, 18, 21, 22, 25, or 30, are considered "antisense oligonucleotides."

Cells that may be used in practicing the methods of the invention include various engineered cells, e.g., transformed host cells, that contain one of the essential nucleic acids described herein. A transformed cell is a cell into which (or into an ancestor of which) has been introduced, by means of recombinant DNA techniques, a nucleic acid encoding one of the essential polypeptides described herein. Both prokaryotic and eukaryotic cells are included, e.g., bacteria, such as Streptococcus, Bacillus, and the like.

Various genetic constructs (e.g., vectors and plasmids) that include one of the essential nucleic acids described herein that is operably linked to a transcription and/or translation sequence to enable expression (e.g., expression vectors) can be used in practicing the methods of the invention. A selected nucleic acid, e.g., a DNA molecule encoding a ylqF polypeptide, is "operably linked" to a transcription and/or translation sequence when it is positioned adjacent to one or more sequence elements, e.g., a promoter, which direct transcription and/or translation of the sequence such that the sequence elements can control transcription and/or translation of the selected nucleic acid.

The terms "protein" and "polypeptide" both refer to any chain of amino acids, regardless of length or post-translational modification (e.g., glycosylation or phosphorylation). Thus, the term ylqF polypeptide, for example, includes full-length, naturally occurring, isolated ylqF proteins, as well as recombinantly or synthetically produced polypeptides that correspond to the full-length, naturally occurring protein, or to a portion of the naturally occurring or synthetic polypeptide.

A purified or isolated compound is a composition that is at least 60% by weight the compound of interest, e.g., a ylqF polypeptide or antibody. Preferably the preparation is at least 75% (e.g., at least 90%, 95%, or even 99%) by weight the compound of interest. Purity can be measured by any appropriate standard method, e.g., column chromatography, polyacrylamide gel electrophoresis, or HPLC analysis.

Preferred polypeptides include a sequence substantially identical to all or a portion of a naturally occurring ylqF, yqeG, yybQ, yerL, or ysxC polypeptide, e.g., including all or a portion of a sequence shown in any of FIGS. 1A–10. Polypeptides "substantially identical" to the essential polypeptides described herein have an amino acid sequence that is at least 80% identical to the amino acid sequence of a polypeptide, represented by SEQ ID NO:2, 5, 8, 11, 14, 17, 20, 23, 26, or 29 (measured as described herein). The new polypeptides can also have a greater percentage identity, e.g., 85%, 90%, 95%, or even higher. For purposes of comparison, the length of the reference polypeptide sequence will generally be at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference polypeptide. Thus, a polypeptide that-is 50% identical to a reference polypeptide that is 100 amino acids long can be a 50 amino acid polypeptide that is completely identical to a 50 amino acid long portion of the reference polypeptide. Alternatively, it can be a 100 amino acid long polypeptide that is 50% identical to the reference polypeptide over its entire length. Of course, other polypeptides also will meet the same criteria.

The methods of the invention also make use of purified or isolated antibodies that specifically bind to one of the essential polypeptides described herein. An antibody "specifically binds" to a particular antigen, e.g., a ylqF polypeptide, when it binds to that antigen, but does not substantially recognize and bind to other molecules in a sample, e.g., a biological sample, that naturally includes a ylqF polypeptide.

The various nucleic acids described herein can be used in a method of obtaining a gene related to an essential gene described herein. Such a method can entail obtaining a labeled probe that includes an isolated nucleic acid which encodes all or a portion of a ylqF nucleic acid, for example, or a homolog thereof; screening a nucleic acid fragment library with the labeled probe under conditions that allow hybridization of the probe to nucleic acid fragments in the library, thereby forming nucleic acid duplexes; isolating labeled duplexes, if any; and preparing a full-length gene sequence from the nucleic acid fragments in any labeled duplex to obtain a gene related to the ylqF gene (e.g., homologs and orthologs of ylqF).

Identification the S-ylqF, S-yqeG, S-yybQ, S-yerL, and S-ysxC Genes

As shown by the experiments described below, the S-ylqF, S-yqeG, S-yybQ, S-yerL, and S-ysxC genes each are essential for survival of *Streptococcus pneumoniae*. *Streptococcus pneumoniae* is available from the ATCC. In general, and for the examples set forth below, each of ylqF, yqeG, yybQ, yerL, and ysxC genes can be identified by creating targeted deletions of genes of interest in a bacterium, e.g., *S. pneumoniae*. The gene of interest was selected as follows. Using standard molecular biology techniques, a library containing fragments of the *Streptococcus pneumoniae* genome was made, using M13 phage or plasmid DNA as the vector. Open reading frames (ORFs) contained within this library were randomly sequenced, using primers that hybridized to the vector. The gene of interest selected for targeted deletion satisfied four criteria, as determined by comparing the sequences with the GenBank database of nucleotide sequences (i) the ORF had no known function; (ii) the ORF had an ortholog in *Bacillus subtilis*; (iii) the ORF was conserved in other bacteria, with $p<10^{-10}$; and (iv) the ORF had no eukaryotic ortholog, with $p>10^{-3}$. The Streptococcus genes S-ylqF, S-yqeG, S-yybQ, S-yerL, and S-ysxC met each of these criteria, suggesting that a compound that inhibited each of these genes or their gene products would have a broad spectrum of antibacterial activity.

Each of these essential genes was, separately, replaced with a nucleic acid sequence conferring resistance to the antibiotic erythromycin (an "erm" gene). Other genetic markers can be used in lieu of this particular antibiotic resistance marker. Polymerase chain reaction (PCR) amplification was used to make a targeted deletion in the Streptococcus genomic DNA, as shown in FIG. 11. Several PCR reactions were used to produce the DNA molecules needed to carry out target deletion of the genes of interest. First, using primers 5 and 6, an erm gene (including coding sequences, promoter sequences, and 5' and 3' untranslated regions) was amplified from the plasmid pIL252 (available from the Bacillus Genetic Stock Center, Columbus, Ohio). Primer 5 consists of 21 nucleotides that are identical to the promoter region of the erm gene and complementary to Sequence A. Primer 5 has the sequence 5'GTG TTC GTG CTG ACT TGC ACC3' (SEQ ID NO:31). Primer 6 consists of 21 nucleotides that are complementary to the 3' end of the erm gene. Primer 6 has the sequence 5'GAA TTA TTT CCT CCC GTT AAA3' (SEQ ID NO:32). PCR amplification of the erm gene was carried out under the following conditions: 30 cycles of 94° C. for 1 minute, 55° C. for 1 minute, and 72° C. for 1.5 minutes, followed by one cycle of 72° C. for 10 minutes.

In the second and third PCR reactions, sequences flanking the gene of interest were amplified and produced as hybrid DNA molecules that also contained a portion of the erm gene. The second reaction produced a double-stranded DNA molecule (termed "Left Flanking Molecule") that includes sequences upstream of the 5' end of the gene of interest and the first 21 nucleotides of the erm gene. As shown in FIG. 11, this reaction utilized primer 1, which is 21 nucleotides in length and identical to a sequence that is located approximately 500 bp upstream of the translation start site of the gene of interest. Primers 1 and 2 are gene-specific and include the sequences 5'GAA AAG TCA TCA TTT GAT GGC3' (SEQ ID NO:33) and 5'GGT GCA AGT CAG CAC GAA CAC CTA GAT AGA GGC AAG CGT GCA3' (SEQ ID NO:34), respectively, for S-ylqF. Primer 2 is 42 nucleotides in length, with 21 of the nucleotides at the 3' end of the primer being complementary to the 5' end of the sense strand of the gene of interest. The 21 nucleotides at the 5' end of the primer were identical to Sequence A and are therefore complementary to the 5' end of the erm gene. Thus, PCR amplification using primers 1 and 2 produced the left flanking DNA molecule, which is a hybrid DNA molecule containing a sequence located upstream of the gene of interest and 21 base pairs of the erm gene, as shown in FIG. 11.

The third PCR reaction was similar to the second reaction, but produced the right flanking DNA molecule, shown in FIG. 11. The right flanking DNA molecule contains 21 base pairs of the 3' end of the erm gene, a 21 base pair portion of the 3' end of the gene of interest, and sequences downstream of the gene of interest. This right flanking DNA molecule was produced with gene-specific primers 3 and 4. For S-ylqF, primers 3 and 4 included the sequences 5'TTT AAC GGG ACG AAA TAA TTC GTC TCT TCG TGA AGG AAG TCC 3' (SEQ ID NO:35) and 5'CTG TGC CAT ATC CTG CAT TAG3' (SEQ ID NO:36), respectively. Primer 3 is 42 nucleotides; the 21 nucleotides at the 5' end of Primer 3 are identical to Sequence B and therefore are identical to the 3' end of the erm gene (including coding sequences, promoter sequences, and 5' and 3' untranslated regions). The 21 nucleotides at the 3' end of Primer 3 are identical to the 3' end of the gene of interest. Primer 4 is 21 nucleotides in length and is complementary to a sequence located approximately 500 bp downstream of the gene of interest. As discussed above, primers 1–4 are gene-specific, and the sequences disclosed above were used for S-ylqF. Gene-specific primers were used to identify the other essential genes described herein, as shown in Table 2.

TABLE 2

Primers Used in Identifying Essential Genes

| Gene | Primer 1 | Primer 2 | Primer 3 | Primer 4 |
|---|---|---|---|---|
| S-ylqF | 5'GAAAAGTCATCA TTTGATGGC3' (SEQ ID NO:33) | 5'GGTGCAAGTCAG CACGAACACCTAGA TAGAGGCAAGCGTGCA3' (SEQ ID NO: 34) | 5'TTTAACGGGAGGAA ATAATTCGTCTCTTCG TGAAGGAAGTCC3' (SEQ ID NO:35) | 5'CTGTGCCATAT CCTGCATTAG3' (SEQ ID NO:36) |

TABLE 2-continued

Primers Used in Identifying Essential Genes

| Gene | Primer 1 | Primer 2 | Primer 3 | Primer 4 |
|---|---|---|---|---|
| S-yqeG | 5'CTTGCTCTATAT CAGTTTGGC3' (SEQ ID NO:37) | 5'GGTGCAAGTCAG CACGAACACGGTTG TTCCAAGCAATGAG GG3' (SEQ ID NO:38) | 5'TTTAACGGGAGGAA ATAATTCATCACTGAA AAGTACGGACCG3' (SEQ ID NO:39) | 5'TTAAGCTGATA GCTCTTAGGC3' (SEQ ID NO:41) |
| S-yybQ | 5'AGCGCCTGCAGT TTGTTTATC3' (SEQ ID NO:41) | 5'GGTGCAAGTCAG CACGAACACCAGAT GACCCGATGGCATC TG3' (SEQ ID NO:42) | 5'TTTAACGGGAGGAA ATAATTCGACAAGGTC GAAGCGGCTTTC3' (SEQ ID NO:43) | 5'CTGGGAGCAGT AGAAACCAGC3' (SEQ ID NO:44) |
| S-yerL | 5'GTCCTCGTGCCC TGGCGTGTC3' (SEQ ID NO:45) | 5'GGTGCAAGTCAG CACGAACACGGCAA CGTGTGTTACCTCT TC3' (SEQ ID NO:46) | 5'TTTAACGGGAGGAA ATAATTCCTAGACAAT GGAGGAGATGCC3' (SEQ ID NO:47) | 5'AGGTTGGCGGA TGGAACCACC3' (SEQ ID NO:48) |
| S-ysxC | 5'CTGTTGCTAGGT ACCGCCTC3' (SEQ ID NO:49) | 5'GGTGCAAGTCAG CACGAACACCCTGC GGATAGTGGGACTT A3' (SEQ ID NO: 50) | 5'TTTAACGGGAGGAA ATAATTCTGACCCAAG TGACGATTTCA3' (SEQ ID NO:51) | 5'CCAGCTGCAAA AACTTAGGC3' (SEQ ID NO:52) |

PCR amplification of the left and right flanking DNA molecules was carried out, separately, in 50 µl reaction mixtures containing: 1 µl Streptococcus pneumoniae (RX1) DNA (0.25 µg), 2.5 µl Primer 1 or Primer 4 (10 pmol/µl), 2.5 µl Primer 2 or Primer 3 (20 pmol/µl), 1.2 µl a mixture dNTPs (10 mM each), 37 µl $H_2O$, 0.7 µl Taq polymerase (5 U/11), and 5 µl 10× Taq polymerase buffer (10 mM Tris, 50 mM KCl, 2.5 mM $MgCl_2$). The left and right flanking DNA molecules were amplified using the following PCR cycling program: 95° C. for 2 minutes; 72° C. for 1 minute; 94° C. for 30 seconds; 49° C. for 30 seconds; 72° C. for 1 minute; repeating the 94° C., 49° C., and 72° C. incubations 30 times; 72° C. for 10 minutes and then stopping the reactions. A 15 µl aliquot of each reaction mixture then was electrophoresed through a 1.2% low melting point agarose gel in TAE buffer and then stained with ethidium bromide. Fragments containing the amplified left and right flanking DNA molecules were excised from the gel and purified using the QIAQUICK™ gel extraction kit (Qiagen, Inc.) Other art-known methods for amplifying and isolating DNA can be substituted. The flanking left and right DNA fragments were eluted into 30 µl TE buffer at pH 8.0.

The amplified erm gene and left and right flanking DNA molecules were then fused together to produce the fusion product, as shown in FIG. 11. The fusion PCR reaction was carried out in a volume of 50 µl containing: 2 µl of each of the left and right flanking DNA molecules and the erm gene PCR product; 5 µl of 10× buffer; 2.5 µl of Primer 1 (10 pmol/µl); 2.5 µl of Primer 4 (10 pmol/µl), 1.2 µl DNTP mix (10 mM each) 32 µl $H_2O$, and 0.7 µl Taq polymerase. The PCR reaction was carried out using the following cycling program: 95° C. for 2 minutes; 72° C. for 1 minute; 94° C. for 30 seconds, 48° C. for 30 seconds; 72° C. for 3 minutes; repeat the 94° C., 48° C. and 72° C. incubations 25 times; 72° C. for 10 minutes. After the reaction was stopped, a 12 µl aliquot of the reaction mixture was electrophoresed through an agarose gel to confirm the presence of a final product of approximately 2 kb.

A 5 µl aliquot of the fusion product was used to transform S. pneumoniae and plated on a medium containing erythromycin in accordance with standard techniques. As shown in FIG. 12, the fusion product and the S. pneumoniae genome undergo a homologous recombination event so that the erm gene replaces the chromosomal copy of the gene of interest, thereby creating a gene knockout. Disruption of an essential gene results in no growth on a medium containing erythromycin. Using this gene knockout method, the ylqF, yqeG, yybQ, yerL, and ysxC genes were each identified as being essential for survival.

Identification of Homologs and Orthologs

Having shown that the ylqF, yqeG, yybQ, yerL, and ysxC genes each are essential for survival of Streptococcus, it can be expected that homologs and orthologs of these genes, when present in other organisms, for example B. subtilis, are essential for survival of those organisms as well. The coding sequences of each gene was used to search the GenBank database of nucleotide sequences, and an ortholog of each sequence was identified in B. subtilis. Sequence comparisons were performed using the Basic Local Alignment Search Tool (BLAST) (Altschul et al., J. Mol. Biol. 215:403–410, 1990). The percent sequence identity shared by the Streptococcus pneumoniae polypeptides and the B. subtilis orthologs was determined using the GAP program from the Genetics Computer Group (GCG) Wisconsin Sequence Analysis Package (Wisconsin Package Version 9.1; Madison, Wis.). The default parameters for gap weight (12) and length weight (4) were used.

Typically, each of the ylqF, yqeG, yybQ, yerL, and ysxC polypeptides and their homologs or orthologs share at least 25% (e.g., at least 30%, 35%, or 40%) sequence identity. Typically, the DNA sequences encoding these essential polypeptides and their homologs or orthologs share at least 20% (e.g., at least 30%, 35%, 40% or 45%) sequence identity. Bioinformatics analysis of each of the ylqF, yqeG, yybQ, yerL, and ysxC genes showed that each of these genes is widely conserved among bacteria. To confirm that the identified orthologs each are essential for survival of B. subtilis, the orthologous genes each were individually deleted from the B. subtilis genome. Such deletion strains have been constructed and do not survive, confirming the essential nature of the polypeptides. The fact that the B-ylqF, B-yqeG, B-yybQ, B-yerL, and B-ysxC genes also are essential for survival suggests that these genes are essential in all bacteria in which they are present. Therefore, an antibacterial drug targeted to any one of these essential genes or gene products is expected to have a broad spectrum of antibacterial activity.

Identification of Essential Genes and Polypeptides in Additional Bacterial Strains and Species Since the *Streptococcus pneumoniae* and *Bacillus subtilis* ylqF, yqeG, yybQ, yerL, and ysxC genes have been identified as being essential for survival, these genes, or fragments thereof, can be used to detect homologous or orthologous genes in yet other organisms (e.g., *E. coli*). In particular, these genes can be used to analyze various pathogenic and non-pathogenic strains of bacteria, particularly gram-positive bacteria. Fragments of a nucleic acid (DNA or RNA) encoding a ylqF polypeptide, for example, (including homologs and orthologs of the sequences listed herein, or sequences complementary thereto) can be used as probes in conventional nucleic acid hybridization assays of nucleic acids from bacteria. For example, nucleic acid probes (which typically are 8–30, or usually 15–20, nucleotides in length) can be used to detect ylqF genes in art-known molecular biology methods, such as Southern blotting, Northern blotting, dot or slot blotting, PCR amplification methods, colony hybridization methods, and the like. Typically, an oligonucleotide probe based on the nucleic acid sequences described herein, or fragment thereof, is labeled and used to screen a genomic library constructed from mRNA obtained from a bacterial strain of interest. A suitable method of labeling involves using polynucleotide kinase to add $^{32}$P-labeled ATP to the oligonucleotide used as the probe. This method is well known in the art, as are several other suitable methods (e.g., biotinylation and enzyme labeling).

Hybridization of the oligonucleotide probe to the library, or other nucleic acid sample, typically is performed under stringent to highly stringent conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming that 1% mismatching results in a 1° C. decrease in the $T_m$, the temperature of the final wash in the hybridization reaction is reduced accordingly (for example, if sequences having ≧95% identity with the probe are sought, the final wash temperature is decreased by 5° C.). In practice, the change in $T_m$ can be between 0.5° C. and 1.5° C. per 1% mismatch.

High stringency hybridization conditions refer to hybridizing at 68° C. in 5× SSC/5× Denhardt's solution/1.0% SDS, and washing in 0.2× SSC/0.1% SDS at 42° C. Stringent conditions refer to washing in 3× SSC at 42° C. The parameters of salt concentration and temperature can be varied to achieve the optimal level of identity between the probe and the target nude-c acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In one approach, libraries constructed from pathogenic or non-pathogenic bacterial strains can be screened. For example, such strains can be screened for expression of ylqF genes by Northern blot analysis. Upon detection of transcripts of a ylqF gene, libraries can be constructed from RNA isolated from the appropriate strain, utilizing standard techniques well known to those of skill in the art. Alternatively, a total genomic DNA library can be screened using a ylqF gene probe. Similar methods can be used to screen for the other essential genes described herein.

New gene sequences can be isolated, for example, by performing PCR using two degenerate oligonucleotide primer pools designed on the basis of nucleotide sequences within the ylqF gene, for example, (including homologs and orthologs of the sequences disclosed herein), as described herein. The template for the reaction can be DNA obtained from strains known to express, or suspected of expressing, a ylqF allele (including alleles of homologs or orthologs of the sequences disclosed herein). The PCR product can be subcloned and sequenced to ensure that the amplified sequences represent the sequences of a new ylqF nucleic acid sequence. Such methods also are suitable for isolating new gene sequences of all of the essential genes disclosed herein.

Synthesis of a ylqF, yqeG, yybQ, yerL, or ysxC polypeptide can readily be accomplished using any of the various art-known techniques. For example, a polypeptide can be synthesized chemically in vitro, or enzymatically (e.g., by in vitro transcription and translation). Alternatively, the gene can be expressed in, and the polypeptide purified from, a cell (e.g., a cultured cell) by using any of the numerous, available gene expression systems. For example, the polypeptide antigen can be produced in a prokaryotic host (e.g., *E. coli* or *B. subtilis*) or in eukaryotic cells, such as yeast cells or in insect cells (e.g., by using a baculovirus-based expression vector).

Proteins and polypeptides can also be produced in plant cells, if desired. For plant cells, viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The optimal methods of transformation or transfection and the choice of expression vehicle will depend on the host system selected. Transformation and transfection methods are described, e.g., in Ausubel et al., supra; expression vehicles may be chosen from those provided, e.g., in *Cloning Vectors*: A Laboratory Manual (P. H. Pouwels et al., 1985, Supp. 1987). The host cells harboring the expression vehicle can be cultured in conventional nutrient media, adapted as needed for activation of a chosen gene, repression of a chosen gene, selection of transformants, or amplification of a chosen gene.

If desired, a ylqF, yqeG, yybQ, yerL, or ysxC polypeptide (including homologs and orthologs of the sequences disclosed herein) can be produced as a fusion protein. For example, the expression vector pUR278 (Ruther et al., *EMBO J.*, 2:1791, 1983) can be used to create lacZ fusion proteins. The art-known pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an exemplary expression system, a baculovirus such as *Autographa californica* nuclear polyhedrosis virus (AcNPV), which grows in *Spodoptera frugiperda* cells, can be used as a vector to express foreign genes. A coding sequence encoding a ylqF polypeptide, for example, can be cloned into a non-essential region (for example the polyhedrin gene) of the viral genome and placed under control of a promoter, e.g., the polyhedrin promoter or an exogenous promoter. Successful insertion of a gene encoding a ylqF polypeptide, for example, can result in inactivation of the polyhedrin gene and production of non-occluded recombinant virus (i.e., virus lacking the proteinaceous coat encoded by the polyhedrin gene). These recombinant viruses are then typically used to infect insect cells (e.g., *Spodoptera frugiperda* cells) in which the inserted gene is expressed (see, e.g., Smith et al., *J. Virol.*, 46:584, 1983; Smith, U.S. Pat. No. 4,215,051). If desired, mammalian cells can be used in lieu of insect cells, provided that the virus is engineered such that the gene encoding the desired polypeptide is placed under the control of a promoter that is active in mammalian cells.

In mammalian host cells, a number of viral-based expression systems can be utilized. When an adenovirus is used as an expression vector, the nucleic acid sequence encoding an essential polypeptide (e.g., ylqF) can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing the desired essential gene product in infected hosts (see, e.g., Logan, Proc. Natl. Acad. Sci. USA, 81:3655, 1984).

Specific initiation signals may be required for efficient translation of inserted nucleic acid sequences. These signals include the ATG initiation codon and adjacent sequences. In general, exogenous translational control signals, including, perhaps, the ATG initiation codon, should be provided. Furthermore, the initiation codon must be in phase with the reading frame of the desired coding sequence to ensure translation of the entire sequence. These exogenous translational control signals and initiation codons can be of a variety of origins, both natural and synthetic. The efficiency of expression may be enhanced by the inclusion of appropriate transcription enhancer elements, or transcription terminators (Bittner et al., *Methods in Enzymol.*, 153:516, 1987).

The ylqF, yqeG, yybQ, yerL, and ysxC polypeptides each can be expressed individually or as fusions with a heterologous polypeptide, such as a signal sequence or other polypeptide having a specific cleavage site at the N-and/or C-terminus of the protein or polypeptide. The heterologous signal sequence selected should be one that is recognized and processed, i.e., cleaved by a signal peptidase, by the host cell in which the fusion protein is expressed.

A host cell can be chosen that modulates the expression of the inserted sequences, or modifies and processes the gene product in a specific, desired fashion. Such modifications and processing (e.g., cleavage) of protein products may facilitate optimal functioning of the protein. Various host cells have characteristic and specific mechanisms for post-translational processing and modification of proteins and gene products. Appropriate cell lines or host systems familiar to those of skill in the art of molecular biology can be chosen to ensure the correct modification and processing of the foreign protein expressed. To this end, eukaryotic host cells that possess the cellular machinery for proper processing of the primary transcript, and phosphorylation of the gene product can be used. Such mammalian host cells include, but are not limited to, CHO, VERO, BHK, HeLa, COS, MDCK, 293, 3T3, WI38, and choroid plexus cell lines.

If desired, the ylqF, yqeG, yybQ, yerL, or ysxC polypeptide (including homologs and orthologs of the sequences described herein) can be produced by a stably-transfected mammalian cell line. A number of vectors suitable for stable transfection of mammalian cells are available to the public, see, e.g., Pouwels et al. (supra); methods for constructing such cell lines are also publicly known, e.g., in Ausubel et al. (supra). In one example, DNA encoding the protein is cloned into an expression vector that includes the dihydrofolate reductase (DHFR) gene. Integration of the vector (including DNA encoding the protein) into the host cell chromosome is selected for by including 0.01–300 µM methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include PCVSEII-DHFR and pAdD26SV(A) (described in Ausubel et al., supra).

A number of other selection systems can be used, including but not limited to, herpes simplex virus thymidine kinase genes, hypoxanthine-guanine phosphoribosyl-transferase genes, and adenine phosphoribosyltransferase genes, which can be employed in tk, hgprt, or aprt cells, respectively. In addition, gpt, which confers resistance to mycophenolic acid (Mulligan et al., *Proc. Natl. Acad. Sci. USA,* 78:2072, 1981); neo, which confers resistance to the aminoglycoside G-418 (Colberre-Garapin et al., *J. Mol. Biol.,* 150:1, 1981); and hygro, which confers resistance to hygromycin (Santerre et al., *Gene,* 30:147, 1981), can be used.

Alternatively, any fusion protein can be readily purified by utilizing an antibody or other molecule that specifically binds the fusion protein being expressed. For example, a system described in Janknecht et al., *Proc. Natl. Acad. Sci. USA,* 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, the ylqF, yqeG, yybQ, yerL, or ysxC polypeptide, or a portion thereof, can be fused to an immunoglobulin Fc domain. Such a fusion protein can be readily purified using a protein A column, for example. Moreover, such fusion proteins permit the production of a chimeric form of the desired essential polypeptide having increased stability in vivo.

Once the recombinant polypeptide is expressed, it can be isolated (i.e., purified). Secreted forms of the polypeptides can be isolated from cell culture media, while non-secreted forms must be isolated from the host cells. Polypeptides can be isolated by affinity chromatography. For example, a ylqF antibody (e.g., produced as described herein) can be attached to a column and used to isolate the protein. Lysis and fractionation of cells harboring the protein prior to affinity chromatography can be performed by standard methods (see, e.g., Ausubel et al., supra). Alternatively, a fusion protein can be constructed and used to isolate the desired essential polypeptide (e.g., a ylqF-maltose binding fusion protein, a ylqF-β-galactosidase fusion protein, or a ylqF-trpE fusion protein; see, e.g., Ausubel et al., supra; New England Biolabs Catalog, Beverly, Mass.). The recombinant protein can, if desired, be further purified, e.g., by high performance liquid chromatography using standard techniques (see, e.g., Fisher, *Laboratory Techniques In Biochemistry And Molecular Biology*, eds., Work and Burdon, Elsevier, 1980). The ylqF, yqeG, yybQ, yerL, or ysxC polypeptides can be used in similar methods.

Given the amino acid sequences described herein, polypeptides useful in practicing the invention, particularly fragments of ylqF, yqeG, yybQ, yerL, and ysxC polypeptides, can be produced by standard chemical synthesis (e.g., by the methods described in *Solid Phase Peptide Synthesis*, 2nd ed., The Pierce Chemical Co., Rockford, Ill., 1984) and used as antigens, for example.

Assay for Antibacterial Agents

The invention provides methods for identifying antibacterial agents. Without being bound by any particular theory as to the biological mechanism involved, the new antibacterial agents are thought to inhibit specifically (1) the function of a ylqF, yqeG, yybQ, yerL, or ysxC polypeptide or (2) expression of a ylqF, yqeG, yybQ, yerL, or ysxC gene. In preferred methods, screening for antibacterial agents is accomplished by identifying those compounds (e.g., small organic molecules) that inhibit the activity of one of the essential polypeptides described herein or the expression of one of the essential genes described herein.

In an exemplary assay, but not the only assay, a promoter that responds to depletion of an essential polypeptide described herein, e.g., ylqF, by upregulation or downregulation is linked to a reporter gene (e.g., β-galactosidase, gus, or GFP), as described above. A bacterial strain containing this reporter gene construct is then exposed to test compounds. Compounds that inhibit the essential polypeptide (or other polypeptides in the essential pathway in which the essential polypeptide participates) will cause a functional depletion of the essential polypeptide and therefore lead to an upregulation or downregulation of expression of the reporter gene. Because the polypeptides described herein are essential for the survival of bacteria, compounds that inhibit the ylqF, yqeG, yybQ, yerL, or ysxC polypeptides in such an assay are expected to be antibacterial agents and can be further tested, if desired, in conventional susceptibility assays.

In other suitable methods, screening for antibacterial agents is accomplished by (i) identifying those compounds that interact with or bind to a ylqF, yqeG, yybQ, yerL, or ysxC polypeptide and (ii) further testing such compounds for their ability to inhibit bacterial growth in vitro or in vivo.

Specific binding of a test compound to a polypeptide can be detected, for example, in vitro by reversibly or irreversibly immobilizing the test compound(s) on a substrate, e.g., the surface of a well of a 96-well polystyrene microtitre plate. Methods for immobilizing polypeptides and other small molecules are well known in the art. For example, the microtitre plates can be coated with a test polypeptide(s), for example, by adding the polypeptide(s) in a solution (typically, at a concentration of 0.05 to 1 mg/ml in a volume of 1–100 μl) to each well, and incubating the plates at room temperature to 37° C. for 0.1 to 36 hours. Polypeptides that are not bound to the plate can be removed by shaking the excess solution from the plate, and then washing the plate (once or repeatedly) with water or a buffer. Typically, the polypeptide is in water or a buffer. The plate is then washed with a buffer that lacks the bound polypeptide. To block the free protein-binding sites on the plates, the plates are blocked with a protein that is unrelated to the bound polypeptide. For example, 300 μl of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate.

The ylqF, yqeG, yybQ, yerL, or ysxC polypeptide (typically 0.05 to 1 mg/ml in 1–100 μl then is allowed to contact the bound substrate at room temperature 37° C. for 0.1 to 36 hours. Excess polypeptide can be removed as described above. Interaction of the test compound with polypeptide can be detected by any of a variety of art-known methods. For example, an antibody that specifically binds a ylqF polypeptide can be used in an immunoassay to detect the ylqF polypeptide. If desired, the antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds the Fc portion of an anti-ylqF antibody). In an alternative detection method, the ylqF polypeptide is labeled, and the label is detected (e.g., by labeling a ylqF polypeptide with a radioisotope, fluorophore, chromophore, or the like). In still another method, the ylqF polypeptide is produced as a fusion protein with a protein that can be detected optically, e.g., green fluorescent protein (which can be detected under UV light). In an alternative method, the polypeptide (e.g., ylqF) can be produced as a fusion protein with an enzyme having a detectable enzymatic activity, such as horse radish peroxidase, alkaline phosphatase, β-galactosidase, or glucose oxidase. Genes encoding all of these enzymes have been cloned and are readily available for use by those of skill in the art. If desired, the fusion protein can include an antigen, and such an antigen can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins).

In various in vivo methods for identifying polypeptides that bind ylqF polypeptides, the conventional two-hybrid assays of protein/protein interactions can be used (see e.g., Chien et al., *Proc. Natl. Acad. Sci. USA*, 88:9578, 1991; Fields et al., U.S. Pat. No. 5,283,173; Fields and Song, *Nature*, 340:245, 1989; Le Douarin et al., *Nucleic Acids Research*, 23:876, 1995; Vidal et al., *Proc. Natl. Acad. Sci. USA*, 93:10315–10320, 1996; and White, *Proc. Natl. Acad. Sci. USA*, 93:10001–10003, 1996). Generally, the two-hybrid methods involve in vivo reconstitution of two separable domains of a transcription factor. One fusion protein contains, for example, a ylqF polypeptide fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the essential polypeptide (e.g., ylqF) to the test polypeptide (i.e., candidate antibacterial agent) reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

The methods described above can be used for high throughput screening of numerous test compounds to identify candidate antibacterial (or anti-bacterial) agents. Having identified a test compound as a candidate antibacterial agent, the candidate antibacterial agent can be further tested for inhibition of bacterial growth in vitro or in vivo (e.g., using an animal, e.g., rodent, model system) if desired. Using other, art-known variations of such methods, one can test the ability of a nucleic acid (e.g., DNA or RNA) used as the test compound to bind ylqF, yqeG, yybQ, yerL, or ysxC.

In vitro, further testing can be accomplished by means known to those in the art such as an enzyme inhibition assay or a whole-cell bacterial growth inhibition assay. For example, an agar dilution assay identifies a substance that inhibits bacterial growth. Microtiter plates are prepared with serial dilutions of the test compound, adding to the preparation a given amount of growth substrate, and providing a preparation of bacteria. Inhibition of bacterial growth is determined, for example, by observing changes in optical densities of the bacterial cultures.

Inhibition of bacterial growth is demonstrated, for example, by comparing (in the presence and absence of a test compound) the rate of growth or the absolute growth of bacterial cells. Inhibition includes a reduction of one of the above measurements by at least 20%. Particularly potent test compounds may further reduce the growth rate (e.g., by at least 25%, 30%, 40%, 50%, 75%, 80%, or 90%).

Rodent (e.g., murine) and rabbit animal models of bacterial infections are known to those of skill in the art, and such animal model systems are accepted for screening antibacterial agents as an indication of their therapeutic efficacy in human patients. In a typical in vivo assay, an animal is infected with a pathogenic strain of bacteria, e.g., by inhalation of bacteria such as *Streptococcus pneumoniae*, and conventional methods and criteria are used to diagnose the mammal as being afflicted with a bacterial infection. The candidate antibacterial agent then is administered to the mammal at a dosage of 1–100 mg/kg of body weight, and the mammal is monitored for signs of amelioration of disease. Alternatively, the test compound can be administered to the mammal prior to infecting the mammal with the bacteria, and the ability of the treated mammal to resist infection is measured of course, the results obtained in the presence of the test compound should be compared with results in control animals, which are not treated with the test compound. Administration of candidate antibacterial agents to the mammal can be carried out as described below, for example.

Pharmaceutical Formulations

Treatment includes administering a pharmaceutically effective amount of a composition containing an antibacterial agent to a subject in need of such treatment, thereby inhibiting bacterial growth in the subject. Such a composition typically contains from about 0.1 to 90% by weight (such as 1 to 20% or 1 to 10%) of an antibacterial agent of the invention in a pharmaceutically acceptable carrier.

Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like) For intravenous injections, water soluble versions of the compounds may be administered by the drip method, whereby a pharmaceutical formulation containing the antibacterial agent and a physiologically acceptable excipient is infused. Physiologically acceptable excipients may include, for example, 5% dextrose, 0.9% saline, Ringer's solution or other suitable excipients. Intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid, (e.g., ethyl oleate).

A topical semi-solid ointment formulation typically contains a concentration of the active ingredient from about 1 to 20%, e.g., 5 to 10%, in a carrier such as a pharmaceutical cream base. Various formulations for topical use include drops, tinctures, lotions, creams, solutions, and ointments containing the active ingredient and various supports and vehicles.

The optimal percentage of the antibacterial agent in each pharmaceutical formulation varies according to the formulation itself and the therapeutic effect desired in the specific pathologies and correlated therapeutic regimens. Appropriate dosages of the antibacterial agents can be readily determined by those of ordinary skill in the art of medicine by monitoring the mammal for signs of disease amelioration or inhibition, and increasing or decreasing the dosage and/or frequency of treatment as desired. The optimal amount of the antibacterial compound used for treatment of conditions caused by or contributed to by bacterial infection may depend upon the manner of administration, the age and the body weight of the subject, and the condition of the subject to be treated. Generally, the antibacterial compound is administered at a dosage of 1 to 100 mg/kg of body weight, and typically at a dosage of 1 to 10 mg/kg of body weight.

Other Embodiments

The methods of the invention also can be practiced with various fragments, variants, analogs, and derivatives of the polypeptides described above that retain one or more of the biological activities of such polypeptides. Naturally-occurring and non-naturally-occurring variants are useful in the invention. Compared with the naturally-occurring gene sequences depicted in FIGS. 1A–10, the nucleic acid sequences encoding variants may have a substitution, deletion, or addition of one or more nucleotides. The preferred variants retain a function of the ylqF, yqeG, yybQ, yerL, or ysxC polypeptide, e.g., as determined in a complementation assay.

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, other art-known assays to detect interactions of test compounds with proteins, or to detect inhibition of bacterial growth also can be used with the ylqF, yqeG, yybQ, yerL, and ysxC genes and gene products (including homologs and orthologs of the sequences disclosed herein). Furthermore, while certain of the methods disclosed herein have been described by using ylqF as an example, it is to be understood that ylqF, yqeG, yybQ, yerL, and ysxC can readily be substituted for ylqF.

SEQUENCE LISTING

<160> NUMBER OF SEQ ID NOS: 52

<210> SEQ ID NO 1
<211> LENGTH: 852
<212> TYPE: DNA
<213> ORGANISM: Streptococcus pneumoniae
<220> FEATURE:
<221> NAME/KEY: CDS
<222> LOCATION: (1)...(849)

<400> SEQUENCE: 1

```
atg gct act att caa tgg ttt cct ggt cac atg tct aaa gct cgt cga      48
Met Ala Thr Ile Gln Trp Phe Pro Gly His Met Ser Lys Ala Arg Arg
  1               5                  10                  15 cag gtg cag gag aat tta aaa ttt gtt gat ttt gtg acg att tta gta      96
Gln Val Gln Glu Asn Leu Lys Phe Val Asp Phe Val Thr Ile Leu Val
             20                  25                  30 gat gca cgc ttg cct cta tct agt caa aat cct atg ttg acc aag att    144
Asp Ala Arg Leu Pro Leu Ser Ser Gln Asn Pro Met Leu Thr Lys Ile
         35                  40                  45 gtt ggt gat aaa cca aaa ctc ttg att tta aac aag gcc gac ttg gct    192
Val Gly Asp Lys Pro Lys Leu Leu Ile Leu Asn Lys Ala Asp Leu Ala
     50                  55                  60 gat cca gca atg acc aag gaa tgg cgt cag tat ttt gaa tca caa gga    240
Asp Pro Ala Met Thr Lys Glu Trp Arg Gln Tyr Phe Glu Ser Gln Gly
 65                  70                  75                  80 atc cag acg cta gct atc aac tcc aaa gag caa gtg act gta aaa gtt    288
Ile Gln Thr Leu Ala Ile Asn Ser Lys Glu Gln Val Thr Val Lys Val
                 85                  90                  95 gta aca gat gcg gcc aag aag ctc atg gct gat aag att gct cgc cag    336
Val Thr Asp Ala Ala Lys Lys Leu Met Ala Asp Lys Ile Ala Arg Gln
            100                 105                 110 aaa gaa cgt ggg att cag att gaa acc ttg cgt act atg att atc ggg    384
Lys Glu Arg Gly Ile Gln Ile Glu Thr Leu Arg Thr Met Ile Ile Gly
        115                 120                 125 att cca aac gct ggt aaa tca act ctg atg aac cgt ttg gct ggt aaa    432
Ile Pro Asn Ala Gly Lys Ser Thr Leu Met Asn Arg Leu Ala Gly Lys
    130                 135                 140 aag att gct gtt gtt gga aac aag cca ggg gtc aca aaa ggt caa caa    480
Lys Ile Ala Val Val Gly Asn Lys Pro Gly Val Thr Lys Gly Gln Gln
145                 150                 155                 160 tgg ctt aaa acc aat aaa gac ctg gaa atc ttg gat aca ccg ggg att    528
Trp Leu Lys Thr Asn Lys Asp Leu Glu Ile Leu Asp Thr Pro Gly Ile
                165                 170                 175 ctc tgg cct aag ttt gag gat gaa act gtt gca ctt aag ttg gca ttg    576
Leu Trp Pro Lys Phe Glu Asp Glu Thr Val Ala Leu Lys Leu Ala Leu
```

```
                    180              185              190
act gga gct atc aaa gac cag ttg ctt cct atg gat gag gtt acc att     624
Thr Gly Ala Ile Lys Asp Gln Leu Leu Pro Met Asp Glu Val Thr Ile
        195              200              205 ttt ggt atc aat tat ttc aaa gaa cat tat cca gaa aag ctg gct gaa     672
Phe Gly Ile Asn Tyr Phe Lys Glu His Tyr Pro Glu Lys Leu Ala Glu
        210              215              220 cgc ttc aaa caa atg aaa att gaa gaa gaa gcg cct gtg att att atg     720
Arg Phe Lys Gln Met Lys Ile Glu Glu Glu Ala Pro Val Ile Ile Met
225              230              235              240 gat atg acc cgc gcc ctc ggt ttc cgt gat gac tat gac cgt ttt tac     768
Asp Met Thr Arg Ala Leu Gly Phe Arg Asp Asp Tyr Asp Arg Phe Tyr
                245              250              255 agt ctc ttc gtg aag gaa gtc cgt gat ggc aaa ctc ggt aac tat acc     816
Ser Leu Phe Val Lys Glu Val Arg Asp Gly Lys Leu Gly Asn Tyr Thr
            260              265              270 tta gat aca ttg gaa gac ctc gat ggc aac gat taa                     852
Leu Asp Thr Leu Glu Asp Leu Asp Gly Asn Asp
        275              280
```

<210> SEQ ID NO 2
<211> LENGTH: 283
<212> TYPE: PRT
<213> ORGANISM: Streptococcus pneumoniae

<400> SEQUENCE: 2

```
Met Ala Thr Ile Gln Trp Phe Pro Gly His Met Ser Lys Ala Arg Arg
1               5                   10                  15

Gln Val Gln Glu Asn Leu Lys Phe Val Asp Phe Val Thr Ile Leu Val
            20                  25                  30

Asp Ala Arg Leu Pro Leu Ser Ser Gln Asn Pro Met Leu Thr Lys Ile
        35                  40                  45

Val Gly Asp Lys Pro Lys Leu Leu Ile Leu Asn Lys Ala Asp Leu Ala
    50                  55                  60

Asp Pro Ala Met Thr Lys Glu Trp Arg Gln Tyr Phe Glu Ser Gln Gly
65                  70                  75                  80

Ile Gln Thr Leu Ala Ile Asn Ser Lys Glu Gln Val Thr Val Lys Val
                85                  90                  95

Val Thr Asp Ala Ala Lys Lys Leu Met Ala Asp Lys Ile Ala Arg Gln
            100                 105                 110

Lys Glu Arg Gly Ile Gln Ile Glu Thr Leu Arg Thr Met Ile Ile Gly
        115                 120                 125

Ile Pro Asn Ala Gly Lys Ser Thr Leu Met Asn Arg Leu Ala Gly Lys
    130                 135                 140

Lys Ile Ala Val Val Gly Asn Lys Pro Gly Val Thr Lys Gly Gln Gln
145                 150                 155                 160

Trp Leu Lys Thr Asn Lys Asp Leu Glu Ile Leu Asp Thr Pro Gly Ile
                165                 170                 175

Leu Trp Pro Lys Phe Glu Asp Glu Thr Val Ala Leu Lys Leu Ala Leu
            180                 185                 190

Thr Gly Ala Ile Lys Asp Gln Leu Leu Pro Met Asp Glu Val Thr Ile
        195                 200                 205

Phe Gly Ile Asn Tyr Phe Lys Glu His Tyr Pro Glu Lys Leu Ala Glu
    210                 215                 220

Arg Phe Lys Gln Met Lys Ile Glu Glu Glu Ala Pro Val Ile Ile Met
225                 230                 235                 240
```

```
Asp Met Thr Arg Ala Leu Gly Phe Arg Asp Asp Tyr Asp Arg Phe Tyr
            245                 250                 255

Ser Leu Phe Val Lys Glu Val Arg Asp Gly Lys Leu Gly Asn Tyr Thr
        260                 265                 270

Leu Asp Thr Leu Glu Asp Leu Asp Gly Asn Asp
        275                 280

<210> SEQ ID NO 3
<211> LENGTH: 852
<212> TYPE: DNA
<213> ORGANISM: Streptococcus pneumoniae

<400> SEQUENCE: 3
ttaatcgttg ccatcgaggt cttccaatgt atctaaggta tagttaccga gtttgccatc    60
acggacttcc ttcacgaaga gactgtaaaa acggtcatag tcatcacgga aaccgagggc   120
gcgggtcata tccataataa tcacaggcgc ttcttcttca attttcattt gtttgaagcg   180
ttcagccagc ttttctggat aatgttcttt gaaataattg ataccaaaaa tggtaacctc   240
atccatagga agcaactggt ctttgatagc tccagtcaat gccaacttaa gtgcaacagt   300
ttcatcctca aacttaggcc agagaatccc cggtgtatcc aagatttcca ggtctttatt   360
ggttttaagc cattgttgac cttttgtgac ccctggcttg tttccaacaa cagcaatctt   420
tttaccagcc aaacggttca tcagagttga tttaccagcg tttggaatcc cgataatcat   480
agtacgcaag gtttcaatct gaatcccacg ttctttctgg cgagcaatct tatcagccat   540
gagcttcttg gccgcatctg ttacaacttt tacagtcact tgctctttgg agttgatagc   600
tagcgtctgg attccttgtg attcaaaata ctgacgccat tccttggtca ttgctggatc   660
agccaagtcg gccttgttta aaatcaagag ttttggttta tcaccaacaa tcttggtcaa   720
cataggattt tgactagata gaggcaagcg tgcatctact aaaatcgtca caaaatcaac   780
aaattttaaa ttctcctgca cctgtcgacg agctttagac atgtgaccag gaaaccattg   840
aatagtagcc at                                                       852

<210> SEQ ID NO 4
<211> LENGTH: 528
<212> TYPE: DNA
<213> ORGANISM: Streptococcus pneumoniae
<220> FEATURE:
<221> NAME/KEY: CDS
<222> LOCATION: (1)...(525)

<400> SEQUENCE: 4 atg gcg att gaa aat tat ata cca gat ttt gct gtg gaa gca gtc tat    48
Met Ala Ile Glu Asn Tyr Ile Pro Asp Phe Ala Val Glu Ala Val Tyr
 1               5                  10                  15 gat ctg aca gtc cca agc ctg cag gcg cag gga ata aag gct gtt ttg    96
Asp Leu Thr Val Pro Ser Leu Gln Ala Gln Gly Ile Lys Ala Val Leu
            20                  25                  30 gtc gat ttg gat aat acc ctc att gct tgg aac aac cct gat gga acg   144
Val Asp Leu Asp Asn Thr Leu Ile Ala Trp Asn Asn Pro Asp Gly Thr
        35                  40                  45 cca gag atg aag caa tgg cta cat gac ctt cgg gac gcg ggt att ggc   192
Pro Glu Met Lys Gln Trp Leu His Asp Leu Arg Asp Ala Gly Ile Gly
    50                  55                  60 att atc gta gtg tca aat aac acc aaa aaa cgc gtt caa cga gca gtt   240
Ile Ile Val Val Ser Asn Asn Thr Lys Lys Arg Val Gln Arg Ala Val
65                  70                  75                  80 gag aaa ttt ggg att gat tac gtt tac tgg gcc ttg aag ccc ttc aca   288
```

```
Glu Lys Phe Gly Ile Asp Tyr Val Tyr Trp Ala Leu Lys Pro Phe Thr
             85                  90                  95 ttt ggt att gac cgt gct atg aag gaa ttc cac tat gac aaa aag gaa       336
Phe Gly Ile Asp Arg Ala Met Lys Glu Phe His Tyr Asp Lys Lys Glu
            100                 105                 110 gtg gtc atg gtt ggt gac caa ctc atg aca gat ata cga gca gcc cac       384
Val Val Met Val Gly Asp Gln Leu Met Thr Asp Ile Arg Ala Ala His
        115                 120                 125 cgt gca ggg att cgg tca att tta gtc aaa ccc ttg gtc caa cat gac       432
Arg Ala Gly Ile Arg Ser Ile Leu Val Lys Pro Leu Val Gln His Asp
    130                 135                 140 tca atc aaa acg cag att aac cga act cgt gag cgt cgt gtt atg aga       480
Ser Ile Lys Thr Gln Ile Asn Arg Thr Arg Glu Arg Arg Val Met Arg
145                 150                 155                 160 aaa atc act gaa aag tac gga ccg att aca tat aaa aaa gga att           525
Lys Ile Thr Glu Lys Tyr Gly Pro Ile Thr Tyr Lys Lys Gly Ile
                165                 170                 175 taa                                                                    528

<210> SEQ ID NO 5
<211> LENGTH: 175
<212> TYPE: PRT
<213> ORGANISM: Streptococcus pneumoniae

<400> SEQUENCE: 5

Met Ala Ile Glu Asn Tyr Ile Pro Asp Phe Ala Val Glu Ala Val Tyr
 1               5                  10                  15

Asp Leu Thr Val Pro Ser Leu Gln Ala Gln Gly Ile Lys Ala Val Leu
                20                  25                  30

Val Asp Leu Asp Asn Thr Leu Ile Ala Trp Asn Asn Pro Asp Gly Thr
            35                  40                  45

Pro Glu Met Lys Gln Trp Leu His Asp Leu Arg Asp Ala Gly Ile Gly
        50                  55                  60

Ile Ile Val Val Ser Asn Asn Thr Lys Lys Arg Val Gln Arg Ala Val
65                  70                  75                  80

Glu Lys Phe Gly Ile Asp Tyr Val Tyr Trp Ala Leu Lys Pro Phe Thr
                85                  90                  95

Phe Gly Ile Asp Arg Ala Met Lys Glu Phe His Tyr Asp Lys Lys Glu
            100                 105                 110

Val Val Met Val Gly Asp Gln Leu Met Thr Asp Ile Arg Ala Ala His
        115                 120                 125

Arg Ala Gly Ile Arg Ser Ile Leu Val Lys Pro Leu Val Gln His Asp
    130                 135                 140

Ser Ile Lys Thr Gln Ile Asn Arg Thr Arg Glu Arg Arg Val Met Arg
145                 150                 155                 160

Lys Ile Thr Glu Lys Tyr Gly Pro Ile Thr Tyr Lys Lys Gly Ile
                165                 170                 175

<210> SEQ ID NO 6
<211> LENGTH: 528
<212> TYPE: DNA
<213> ORGANISM: Streptococcus pneumoniae

<400> SEQUENCE: 6
ttaaattcct tttttatatg taatcggtcc gtacttttca gtgattttc tcataacacg        60 acgctcacga gttcggttaa tctgcgtttt gattgagtca tgttggacca agggtttgac       120
taaaattgac cgaatccctg cacggtgggc tgctcgtata tctgtcatga gttggtcacc       180
```

-continued

```
aaccatgacc acttccttt tgtcatagtg gaattccttc atagcacggt caataccaaa    240
tgtgaagggc ttcaaggccc agtaaacgta atcaatccca aatttctcaa ctgctcgttg    300
aacgcgtttt ttggtgttat ttgacactac gataatgcca atacccgcgt cccgaaggtc    360
atgtagccat tgcttcatct ctggcgttcc atcaggttg ttccaagcaa tgagggtatt    420
atccaaatcg accaaaacag cctttattcc ctgcgcctgc aggcttggga ctgtcagatc    480
atagactgct tccacagcaa aatctggtat ataattttca atcgccat                 528
```

<210> SEQ ID NO 7
<211> LENGTH: 936
<212> TYPE: DNA
<213> ORGANISM: Streptococcus pneumoniae
<220> FEATURE:
<221> NAME/KEY: CDS
<222> LOCATION: (1)...(933)

<400> SEQUENCE: 7

```
atg tcc aag att cta gta ttt ggt cac caa aat cca gac tca gat gcc    48
Met Ser Lys Ile Leu Val Phe Gly His Gln Asn Pro Asp Ser Asp Ala
 1               5                  10                  15 atc ggg tca tct gta gct ttt gcc tac ctt gca aaa gaa gct tac ggt    96
Ile Gly Ser Ser Val Ala Phe Ala Tyr Leu Ala Lys Glu Ala Tyr Gly
            20                  25                  30 ttg gat acg gaa gct gtt gcc ctt gga act cca aat gaa gaa aca gcc   144
Leu Asp Thr Glu Ala Val Ala Leu Gly Thr Pro Asn Glu Glu Thr Ala
        35                  40                  45 ttt gtc ttg aac tat ttt ggt gtg gaa gca cca cgt gtt atc act tct   192
Phe Val Leu Asn Tyr Phe Gly Val Glu Ala Pro Arg Val Ile Thr Ser
    50                  55                  60 gcc aaa gca gag ggg gca gag caa gtt atc ttg act gac cac aat gaa   240
Ala Lys Ala Glu Gly Ala Glu Gln Val Ile Leu Thr Asp His Asn Glu
65                  70                  75                  80 ttc caa caa tct gta tca gat atc gct gaa gta gaa gtt tac ggt gtt   288
Phe Gln Gln Ser Val Ser Asp Ile Ala Glu Val Glu Val Tyr Gly Val
                85                  90                  95 gta gac cac cac cgt gtg gct aac ttt gaa act gca agc cca ctt tac   336
Val Asp His His Arg Val Ala Asn Phe Glu Thr Ala Ser Pro Leu Tyr
            100                 105                 110 atg cgt ttg gag cca gtt gga tca gcg tct tca atc gtt tac cgt atg   384
Met Arg Leu Glu Pro Val Gly Ser Ala Ser Ser Ile Val Tyr Arg Met
        115                 120                 125 ttc aaa gaa cat ggt gta gct gtg cct aaa gag att gca ggt ttg atg   432
Phe Lys Glu His Gly Val Ala Val Pro Lys Glu Ile Ala Gly Leu Met
    130                 135                 140 ctt tca ggt ttg att tca gat acc ctt ctt ttg aaa tca cca aca aca   480
Leu Ser Gly Leu Ile Ser Asp Thr Leu Leu Leu Lys Ser Pro Thr Thr
145                 150                 155                 160 cac cca aca gat aaa atc att gct cct gaa ttg gct gaa ttg gct ggt   528
His Pro Thr Asp Lys Ile Ile Ala Pro Glu Leu Ala Glu Leu Ala Gly
                165                 170                 175 gta aac ttg gaa gaa tat ggt ttg gca atg ttg aaa gct ggt acc aac   576
Val Asn Leu Glu Glu Tyr Gly Leu Ala Met Leu Lys Ala Gly Thr Asn
            180                 185                 190 ttg gct agc aaa tct gct gaa gaa ttg att gac atc gat gct aag act   624
Leu Ala Ser Lys Ser Ala Glu Glu Leu Ile Asp Ile Asp Ala Lys Thr
        195                 200                 205 ttt gaa ctc aac gga aat aat gtc cgt gtt gcc caa gtg aac aca gtt   672
Phe Glu Leu Asn Gly Asn Asn Val Arg Val Ala Gln Val Asn Thr Val
    210                 215                 220
```

```
gac atc gct gaa gtt ttg gaa cgc caa gca gaa att gaa gct gca atg      720
Asp Ile Ala Glu Val Leu Glu Arg Gln Ala Glu Ile Glu Ala Ala Met
225                 230                 235                 240 caa gct gcc aac gaa tca aac ggc tac tct gac ttt gtc ttg atg att      768
Gln Ala Ala Asn Glu Ser Asn Gly Tyr Ser Asp Phe Val Leu Met Ile
            245                 250                 255 aca gat atc gtc aac tca aac tca gaa ata ttg gct ctt ggt gcc aat      816
Thr Asp Ile Val Asn Ser Asn Ser Glu Ile Leu Ala Leu Gly Ala Asn
        260                 265                 270 atg gac aag gtc gaa gcg gct ttc aat ttc aaa ctt gaa aac aat cat      864
Met Asp Lys Val Glu Ala Ala Phe Asn Phe Lys Leu Glu Asn Asn His
    275                 280                 285 gcc ttc ctt gct ggt gcc gtt tca cgt aag aaa caa gtg gta cct caa      912
Ala Phe Leu Ala Gly Ala Val Ser Arg Lys Lys Gln Val Val Pro Gln
290                 295                 300 tta act gaa agc ttt aat gcg taa                                      936
Leu Thr Glu Ser Phe Asn Ala
305                 310

<210> SEQ ID NO 8
<211> LENGTH: 311
<212> TYPE: PRT
<213> ORGANISM: Streptococcus pneumoniae

<400> SEQUENCE: 8

Met Ser Lys Ile Leu Val Phe Gly His Gln Asn Pro Asp Ser Asp Ala
1               5                   10                  15

Ile Gly Ser Ser Val Ala Phe Ala Tyr Leu Ala Lys Glu Ala Tyr Gly
            20                  25                  30

Leu Asp Thr Glu Ala Val Ala Leu Gly Thr Pro Asn Glu Glu Thr Ala
        35                  40                  45

Phe Val Leu Asn Tyr Phe Gly Val Glu Ala Pro Arg Val Ile Thr Ser
    50                  55                  60

Ala Lys Ala Glu Gly Ala Glu Gln Val Ile Leu Thr Asp His Asn Glu
65                  70                  75                  80

Phe Gln Gln Ser Val Ser Asp Ile Ala Glu Val Glu Val Tyr Gly Val
                85                  90                  95

Val Asp His His Arg Val Ala Asn Phe Glu Thr Ala Ser Pro Leu Tyr
            100                 105                 110

Met Arg Leu Glu Pro Val Gly Ser Ala Ser Ser Ile Val Tyr Arg Met
        115                 120                 125

Phe Lys Glu His Gly Val Ala Val Pro Lys Glu Ile Ala Gly Leu Met
    130                 135                 140

Leu Ser Gly Leu Ile Ser Asp Thr Leu Leu Lys Ser Pro Thr Thr
145                 150                 155                 160

His Pro Thr Asp Lys Ile Ile Ala Pro Glu Leu Ala Glu Leu Ala Gly
                165                 170                 175

Val Asn Leu Glu Glu Tyr Gly Leu Ala Met Leu Lys Ala Gly Thr Asn
            180                 185                 190

Leu Ala Ser Lys Ser Ala Glu Leu Ile Asp Ile Asp Ala Lys Thr
        195                 200                 205

Phe Glu Leu Asn Gly Asn Asn Val Arg Val Ala Gln Val Asn Thr Val
    210                 215                 220

Asp Ile Ala Glu Val Leu Glu Arg Gln Ala Glu Ile Glu Ala Ala Met
225                 230                 235                 240

Gln Ala Ala Asn Glu Ser Asn Gly Tyr Ser Asp Phe Val Leu Met Ile
```

-continued

```
               245                 250                 255
Thr Asp Ile Val Asn Ser Asn Ser Glu Ile Leu Ala Leu Gly Ala Asn
            260                 265                 270

Met Asp Lys Val Glu Ala Ala Phe Asn Phe Lys Leu Glu Asn Asn His
        275                 280                 285

Ala Phe Leu Ala Gly Ala Val Ser Arg Lys Lys Gln Val Val Pro Gln
    290                 295                 300

Leu Thr Glu Ser Phe Asn Ala
305                 310
```

<210> SEQ ID NO 9
<211> LENGTH: 936
<212> TYPE: DNA
<213> ORGANISM: Streptococcus pneumoniae

<400> SEQUENCE: 9

| | | | | | |
|---|---|---|---|---|---|
| ttacgcatta | aagctttcag | ttaattgagg | taccacttgt | ttcttacgtg | aaacggcacc | 60 |
| agcaaggaag | gcatgattgt | tttcaagttt | gaaattgaaa | gccgcttcga | ccttgtccat | 120 |
| attggcacca | agagccaata | tttctgagtt | tgagttgacg | atatctgtaa | tcatcaagac | 180 |
| aaagtcagag | tagccgtttg | attcgttggc | agcttgcatt | gcagcttcaa | tttctgcttg | 240 |
| gcgttccaaa | acttcagcga | tgtcaactgt | gttcacttgg | gcaacacgga | cattatttcc | 300 |
| gttgagttca | aaagtcttag | catcgatgtc | aatcaattct | tcagcagatt | tgctagccaa | 360 |
| gttggtacca | gctttcaaca | ttgccaaacc | atattcttcc | aagtttacac | cagccaattc | 420 |
| agccaattca | ggagcaatga | ttttatctgt | tgggtgtgtt | gttggtgatt | tcaaaagaag | 480 |
| ggtatctgaa | atcaaacctg | aaagcatcaa | acctgcaatc | tctttaggca | cagctacacc | 540 |
| atgttctttg | aacatacggt | aaacgattga | agacgctgat | ccaactggct | ccaaacgcat | 600 |
| gtaaagtggg | cttgcagttt | caagttagc | cacacggtgg | tggtctacaa | caccgtaaac | 660 |
| ttctacttca | gcgatatctg | atacagattg | ttggaattca | ttgtggtcag | tcaagataac | 720 |
| ttgctctgcc | ccctctgctt | tggcagaagt | gataacacgt | ggtgcttcca | caccaaaata | 780 |
| gttcaagaca | aaggctgttt | cttcatttgg | agttccaagg | gcaacagctt | ccgtatccaa | 840 |
| accgtaagct | tcttttgcaa | ggtaggcaaa | agctacagat | gacccgatgg | catctgagtc | 900 |
| tggattttgg | tgaccaaata | ctagaatctt | ggacat | | | 936 |

<210> SEQ ID NO 10
<211> LENGTH: 303
<212> TYPE: DNA
<213> ORGANISM: Streptococcus pneumoniae
<220> FEATURE:
<221> NAME/KEY: CDS
<222> LOCATION: (1)...(300)

<400> SEQUENCE: 10

```
atg aaa att acg caa gaa gag gta aca cac gtt gcc aat ctt tca aaa      48
Met Lys Ile Thr Gln Glu Glu Val Thr His Val Ala Asn Leu Ser Lys
 1               5                  10                  15 tta aga ttc tct gaa gaa gaa act gct gcc ttt gcg acc acc ttg tct      96
Leu Arg Phe Ser Glu Glu Glu Thr Ala Ala Phe Ala Thr Thr Leu Ser
            20                  25                  30 aag att gtt gac atg gtt gaa ttg ctg ggc gaa gtt gac aca act ggt     144
Lys Ile Val Asp Met Val Glu Leu Leu Gly Glu Val Asp Thr Thr Gly
        35                  40                  45 gtc gca cct act acg act atg gct gac cgc aag act gta ctc cgc cct     192
Val Ala Pro Thr Thr Thr Met Ala Asp Arg Lys Thr Val Leu Arg Pro
```

|  |  |  |  |  |  |  |  |  |  |  |  |  |  |  |  |  |
|---|---|---|---|---|---|---|---|---|---|---|---|---|---|---|---|---|
|  | 50 |  |  |  | 55 |  |  |  | 60 |  |  |  |  |  |  |  |
| gat | gtg | gcc | gaa | gaa | gga | ata | gac | cgt | gat | cgc | ttg | ttt | aaa | aac | gta | 240 |
| Asp | Val | Ala | Glu | Glu | Gly | Ile | Asp | Arg | Asp | Arg | Leu | Phe | Lys | Asn | Val |  |
|  | 65 |  |  |  | 70 |  |  |  | 75 |  |  |  | 80 |  |  |  |
| cct | gaa | aaa | gac | aac | tac | tat | atc | aag | gtg | cca | gct | atc | cta | gac | aat | 288 |
| Pro | Glu | Lys | Asp | Asn | Tyr | Tyr | Ile | Lys | Val | Pro | Ala | Ile | Leu | Asp | Asn |  |
|  |  |  |  | 85 |  |  |  |  | 90 |  |  |  |  | 95 |  |  |
| gga | gga | gat | gcc | taa |  |  |  |  |  |  |  |  |  |  |  | 303 |
| Gly | Gly | Asp | Ala |  |  |  |  |  |  |  |  |  |  |  |  |  |
|  |  |  | 100 |  |  |  |  |  |  |  |  |  |  |  |  |  |

<210> SEQ ID NO 11
<211> LENGTH: 100
<212> TYPE: PRT
<213> ORGANISM: Streptococcus pneumoniae

<400> SEQUENCE: 11

Met Lys Ile Thr Gln Glu Glu Val Thr His Val Ala Asn Leu Ser Lys
 1               5                  10                  15

Leu Arg Phe Ser Glu Glu Glu Thr Ala Ala Phe Ala Thr Thr Leu Ser
             20                  25                  30

Lys Ile Val Asp Met Val Glu Leu Leu Gly Glu Val Asp Thr Thr Gly
         35                  40                  45

Val Ala Pro Thr Thr Thr Met Ala Asp Arg Lys Thr Val Leu Arg Pro
     50                  55                  60

Asp Val Ala Glu Glu Gly Ile Asp Arg Asp Arg Leu Phe Lys Asn Val
 65                  70                  75                  80

Pro Glu Lys Asp Asn Tyr Tyr Ile Lys Val Pro Ala Ile Leu Asp Asn
                 85                  90                  95

Gly Gly Asp Ala
            100

<210> SEQ ID NO 12
<211> LENGTH: 303
<212> TYPE: DNA
<213> ORGANISM: Streptococcus pneumoniae

<400> SEQUENCE: 12
ttaggcatct cctccattgt ctaggatagc tggcaccttg atatagtagt tgtcttttc       60 aggtacgttt ttaaacaagc gatcacggtc tattccttct tcggccacat cagggcggag    120
tacagtcttg cggtcagcca tagtcgtagt aggtgcgaca ccagttgtgt caacttcgcc    180
cagcaattca accatgtcaa caatcttaga caaggtggtc gcaaaggcag cagtttcttc    240
ttcagagaat cttaattttg aaagattggc aacgtgtgtt acctcttctt gcgtaatttt    300
cat                                                                  303

<210> SEQ ID NO 13
<211> LENGTH: 588
<212> TYPE: DNA
<213> ORGANISM: Streptococcus pneumoniae
<220> FEATURE:
<221> NAME/KEY: CDS
<222> LOCATION: (1)...(585)

<400> SEQUENCE: 13

| atg | gaa | ctt | aat | aca | cac | aat | gct | gaa | atc | ttg | ctc | agt | gca | gct | aat | 48 |
|---|---|---|---|---|---|---|---|---|---|---|---|---|---|---|---|---|
| Met | Glu | Leu | Asn | Thr | His | Asn | Ala | Glu | Ile | Leu | Leu | Ser | Ala | Ala | Asn |  |
|  1  |     |     |     |  5  |     |     |     |     | 10  |     |     |     |     | 15  |     |  |
| aag | tcc | cac | tat | ccg | cag | gat | gaa | ctg | cca | gag | att | gcc | cta | gca | ggg | 96 |

```
Lys Ser His Tyr Pro Gln Asp Glu Leu Pro Glu Ile Ala Leu Ala Gly
            20                  25                  30 cgt tca aat gtt ggt aaa tcc agc ttt atc aac act atg ttg aac cgt      144
Arg Ser Asn Val Gly Lys Ser Ser Phe Ile Asn Thr Met Leu Asn Arg
        35                  40                  45 aag aat ctc gcc cgt aca tca gga aaa cct ggt aaa acc cag ctc ctg      192
Lys Asn Leu Ala Arg Thr Ser Gly Lys Pro Gly Lys Thr Gln Leu Leu
    50                  55                  60 aac ttt ttt aac att gat gac aag atg cgc ttt gtg gat gtg cct ggt      240
Asn Phe Phe Asn Ile Asp Asp Lys Met Arg Phe Val Asp Val Pro Gly
65                  70                  75                  80 tat ggc tat gct cgt gtt tct aaa aag gaa cgt gaa aag tgg ggg tgc      288
Tyr Gly Tyr Ala Arg Val Ser Lys Lys Glu Arg Glu Lys Trp Gly Cys
                85                  90                  95 atg att gag gag tac tta acg act cgg gaa aat ctc cgt gcg gtt gtc      336
Met Ile Glu Glu Tyr Leu Thr Thr Arg Glu Asn Leu Arg Ala Val Val
            100                 105                 110 agt cta gtt gac ctt cgt cat gac ccg tca gca gat gat gtg cag atg      384
Ser Leu Val Asp Leu Arg His Asp Pro Ser Ala Asp Asp Val Gln Met
        115                 120                 125 tac gaa ttt ctc aag tat tat gag att cca gtc atc att gtg gcg acc      432
Tyr Glu Phe Leu Lys Tyr Tyr Glu Ile Pro Val Ile Ile Val Ala Thr
    130                 135                 140 aag gcg gac aag att cct cgt ggt aaa tgg aac aag cat gaa tca gca      480
Lys Ala Asp Lys Ile Pro Arg Gly Lys Trp Asn Lys His Glu Ser Ala
145                 150                 155                 160 atc aaa aag aaa tta aac ttt gac ccg agt gac gat ttc atc ctc ttt      528
Ile Lys Lys Lys Leu Asn Phe Asp Pro Ser Asp Asp Phe Ile Leu Phe
                165                 170                 175 tca tct gtc agt aag gca ggg atg gat gag gct tgg gat gca atc tta      576
Ser Ser Val Ser Lys Ala Gly Met Asp Glu Ala Trp Asp Ala Ile Leu
            180                 185                 190 gaa aaa ttg tga                                                      588
Glu Lys Leu
        195

<210> SEQ ID NO 14
<211> LENGTH: 195
<212> TYPE: PRT
<213> ORGANISM: Streptococcus pneumoniae

<400> SEQUENCE: 14

Met Glu Leu Asn Thr His Asn Ala Glu Ile Leu Leu Ser Ala Ala Asn
1               5                   10                  15

Lys Ser His Tyr Pro Gln Asp Glu Leu Pro Glu Ile Ala Leu Ala Gly
            20                  25                  30

Arg Ser Asn Val Gly Lys Ser Ser Phe Ile Asn Thr Met Leu Asn Arg
        35                  40                  45

Lys Asn Leu Ala Arg Thr Ser Gly Lys Pro Gly Lys Thr Gln Leu Leu
    50                  55                  60

Asn Phe Phe Asn Ile Asp Asp Lys Met Arg Phe Val Asp Val Pro Gly
65                  70                  75                  80

Tyr Gly Tyr Ala Arg Val Ser Lys Lys Glu Arg Glu Lys Trp Gly Cys
                85                  90                  95

Met Ile Glu Glu Tyr Leu Thr Thr Arg Glu Asn Leu Arg Ala Val Val
            100                 105                 110

Ser Leu Val Asp Leu Arg His Asp Pro Ser Ala Asp Asp Val Gln Met
        115                 120                 125
```

```
                    Tyr Glu Phe Leu Lys Tyr Tyr Glu Ile Pro Val Ile Ile Val Ala Thr
                        130                 135                 140

Lys Ala Asp Lys Ile Pro Arg Gly Lys Trp Asn Lys His Glu Ser Ala
                    145                 150                 155                 160

Ile Lys Lys Lys Leu Asn Phe Asp Pro Ser Asp Phe Ile Leu Phe
                                    165                 170                 175

Ser Ser Val Ser Lys Ala Gly Met Asp Glu Ala Trp Asp Ala Ile Leu
                                180                 185                 190

Glu Lys Leu
                            195

<210> SEQ ID NO 15
<211> LENGTH: 588
<212> TYPE: DNA
<213> ORGANISM: Streptococcus pneumoniae

<400> SEQUENCE: 15 tcacaattt tctaagattg catcccaagc ctcatccatc cctgccttac tgacagatga      60
aaagaggatg aaatcgtcac tcgggtcaaa gtttaatttc tttttgattg ctgattcatg    120
cttgttccat ttaccacgag gaatcttgtc cgccttggtc gccacaatga tgactggaat    180
ctcataatac ttgagaaatt cgtacatctg cacatcatct gctgacgggt catgacgaag    240
gtcaactaga ctgacaaccg cacggagatt tcccgagtc gttaagtact cctcaatcat     300
gcacccccac ttttcacgtt cctttttaga aacacgagca tagccataac caggcacatc    360
cacaaagcgc atcttgtcat caatgttaaa aaagttcagg agctgggttt taccaggttt    420
tcctgatgta cgggcgagat tcttacggtt caacatagtg ttgataaagc tggatttacc    480
aacatttgaa cgccctgcta gggcaatctc tggcagttca tcctgcggat agtgggactt    540
attagctgca ctgagcaaga tttcagcatt gtgtgtatta agttccat                588

<210> SEQ ID NO 16
<211> LENGTH: 846
<212> TYPE: DNA
<213> ORGANISM: Bacillus subtilis
<220> FEATURE:
<221> NAME/KEY: CDS
<222> LOCATION: (1)...(846)

<400> SEQUENCE: 16 atg aca att caa tgg ttc ccg ggc cat atg gca aaa gca aga agg gaa     48
Met Thr Ile Gln Trp Phe Pro Gly His Met Ala Lys Ala Arg Arg Glu
  1               5                  10                  15 gta acc gaa aaa tta aaa tta atc gat atc gta tat gaa ttg gta gat     96
Val Thr Glu Lys Leu Lys Leu Ile Asp Ile Val Tyr Glu Leu Val Asp
             20                  25                  30 gcc aga att cca atg tca tca aga aac cca atg att gaa gat att cta    144
Ala Arg Ile Pro Met Ser Ser Arg Asn Pro Met Ile Glu Asp Ile Leu
         35                  40                  45 aaa aac aag ccg cga att atg ctg tta aac aag gct gac aaa gca gat    192
Lys Asn Lys Pro Arg Ile Met Leu Leu Asn Lys Ala Asp Lys Ala Asp
     50                  55                  60 gcg gca gtt aca cag cag tgg aaa gag cac ttt gag aac cag ggg atc    240
Ala Ala Val Thr Gln Gln Trp Lys Glu His Phe Glu Asn Gln Gly Ile
 65                  70                  75                  80 cgc tct ctg tct att aat tct gta aat gga caa ggg tta aat caa att    288
Arg Ser Leu Ser Ile Asn Ser Val Asn Gly Gln Gly Leu Asn Gln Ile
                 85                  90                  95 gtg cct gca tca aaa gag atc ctc caa gaa aaa ttt gac cgg atg cgt    336
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Val | Pro | Ala | Ser | Lys | Glu | Ile | Leu | Gln | Glu | Lys | Phe | Asp | Arg | Met | Arg |  |
|     |     |     | 100 |     |     |     | 105 |     |     |     | 110 |     |     |     |     |  |

```
gcg aaa ggt gtg aag ccg aga gcg att cgc gct ttg att atc ggc att       384
Ala Lys Gly Val Lys Pro Arg Ala Ile Arg Ala Leu Ile Ile Gly Ile
        115                 120                 125 cca aac gtc gga aaa tca acg ctc atc aac cgg ctt gca aag aaa aac       432
Pro Asn Val Gly Lys Ser Thr Leu Ile Asn Arg Leu Ala Lys Lys Asn
130                 135                 140 ata gca aaa acg gga gac aga cct ggt att acg act tct caa cag tgg       480
Ile Ala Lys Thr Gly Asp Arg Pro Gly Ile Thr Thr Ser Gln Gln Trp
145                 150                 155                 160 gtc aaa gtt ggg aaa gaa tta gag cta tta gat aca ccg gga att ttg       528
Val Lys Val Gly Lys Glu Leu Glu Leu Leu Asp Thr Pro Gly Ile Leu
                165                 170                 175 tgg cct aaa ttt gag gat gag ctt gtc ggt ttg aga ctg gca gtc acc       576
Trp Pro Lys Phe Glu Asp Glu Leu Val Gly Leu Arg Leu Ala Val Thr
            180                 185                 190 ggg gct att aaa gac tcg att atc aat ttg cag gac gtg gcc gtg ttt       624
Gly Ala Ile Lys Asp Ser Ile Ile Asn Leu Gln Asp Val Ala Val Phe
        195                 200                 205 ggt ctt cgt ttt ctc gaa gaa cat tac cca gaa cgg ctt aaa gag cgt       672
Gly Leu Arg Phe Leu Glu Glu His Tyr Pro Glu Arg Leu Lys Glu Arg
    210                 215                 220 tat ggc ctt gat gag atc cca gag gac att gcc gag ctg ttt gat gca       720
Tyr Gly Leu Asp Glu Ile Pro Glu Asp Ile Ala Glu Leu Phe Asp Ala
225                 230                 235                 240 ata ggt gaa aag cgg ggc tgt ctc atg agc ggt ggg ctc atc aac tac       768
Ile Gly Glu Lys Arg Gly Cys Leu Met Ser Gly Gly Leu Ile Asn Tyr
                245                 250                 255 gat aag acg act gaa gtc atc att cgc gat att cgc act gaa aag ttc       816
Asp Lys Thr Thr Glu Val Ile Ile Arg Asp Ile Arg Thr Glu Lys Phe
            260                 265                 270 ggc agg ctg tca ttt gaa cag ccg acg atg                               846
Gly Arg Leu Ser Phe Glu Gln Pro Thr Met
        275                 280
```

<210> SEQ ID NO 17
<211> LENGTH: 282
<212> TYPE: PRT
<213> ORGANISM: Bacillus subtilis

<400> SEQUENCE: 17

|     |     |     |     |     |     |     |     |     |     |     |     |     |     |     |
| --- | --- | --- | --- | --- | --- | --- | --- | --- | --- | --- | --- | --- | --- | --- |
| Met | Thr | Ile | Gln | Trp | Phe | Pro | Gly | His | Met | Ala | Lys | Ala | Arg | Arg | Glu |
| 1   |     |     |     | 5   |     |     |     |     | 10  |     |     |     |     | 15  |     |
| Val | Thr | Glu | Lys | Leu | Lys | Leu | Ile | Asp | Ile | Val | Tyr | Glu | Leu | Val | Asp |
|     |     |     | 20  |     |     |     |     | 25  |     |     |     |     | 30  |     |     |
| Ala | Arg | Ile | Pro | Met | Ser | Ser | Arg | Asn | Pro | Met | Ile | Glu | Asp | Ile | Leu |
|     |     | 35  |     |     |     |     | 40  |     |     |     |     | 45  |     |     |     |
| Lys | Asn | Lys | Pro | Arg | Ile | Met | Leu | Leu | Asn | Lys | Ala | Asp | Lys | Ala | Asp |
|     | 50  |     |     |     |     | 55  |     |     |     |     | 60  |     |     |     |     |
| Ala | Ala | Val | Thr | Gln | Gln | Trp | Lys | Glu | His | Phe | Glu | Asn | Gln | Gly | Ile |
| 65  |     |     |     |     | 70  |     |     |     |     | 75  |     |     |     |     | 80  |
| Arg | Ser | Leu | Ser | Ile | Asn | Ser | Val | Asn | Gly | Gln | Gly | Leu | Asn | Gln | Ile |
|     |     |     |     | 85  |     |     |     |     | 90  |     |     |     |     | 95  |     |
| Val | Pro | Ala | Ser | Lys | Glu | Ile | Leu | Gln | Glu | Lys | Phe | Asp | Arg | Met | Arg |
|     |     |     | 100 |     |     |     |     | 105 |     |     |     | 110 |     |     |     |
| Ala | Lys | Gly | Val | Lys | Pro | Arg | Ala | Ile | Arg | Ala | Leu | Ile | Ile | Gly | Ile |
|     |     | 115 |     |     |     |     | 120 |     |     |     |     | 125 |     |     |     |

```
Pro Asn Val Gly Lys Ser Thr Leu Ile Asn Arg Leu Ala Lys Lys Asn
    130                 135                 140

Ile Ala Lys Thr Gly Asp Arg Pro Gly Ile Thr Thr Ser Gln Gln Trp
145                 150                 155                 160

Val Lys Val Gly Lys Glu Leu Glu Leu Leu Asp Thr Pro Gly Ile Leu
                165                 170                 175

Trp Pro Lys Phe Glu Asp Glu Leu Val Gly Leu Arg Leu Ala Val Thr
            180                 185                 190

Gly Ala Ile Lys Asp Ser Ile Ile Asn Leu Gln Asp Val Ala Val Phe
        195                 200                 205

Gly Leu Arg Phe Leu Glu Glu His Tyr Pro Glu Arg Leu Lys Glu Arg
    210                 215                 220

Tyr Gly Leu Asp Glu Ile Pro Glu Asp Ile Ala Glu Leu Phe Asp Ala
225                 230                 235                 240

Ile Gly Glu Lys Arg Gly Cys Leu Met Ser Gly Leu Ile Asn Tyr
                245                 250                 255

Asp Lys Thr Thr Glu Val Ile Ile Arg Asp Ile Arg Thr Glu Lys Phe
            260                 265                 270

Gly Arg Leu Ser Phe Glu Gln Pro Thr Met
        275                 280

<210> SEQ ID NO 18
<211> LENGTH: 846
<212> TYPE: DNA
<213> ORGANISM: Bacillus subtilis

<400> SEQUENCE: 18
catcgtcggc tgttcaaatg acagcctgcc gaacttttca gtgcgaatat cgcgaatgat      60
gacttcagtc gtcttatcgt agttgatgag cccaccgctc atgagacagc cccgcttttc     120
acctattgca tcaaacagct cggcaatgtc ctctgggatc tcatcaaggc cataacgctc     180
tttaagccgt tctgggtaat gttcttcgag aaaacgaaga ccaaacacgg ccacgtcctg     240
caaattgata tcgagtctt taatagcccc ggtgactgcc agtctcaaac cgacaagctc     300
atcctcaaat ttaggccaca aaattcccgg tgtatctaat agctctaatt ctttcccaac     360
tttgacccac tgttgagaag tcgtaatacc aggtctgtct cccgtttttg ctatgttttt     420 cttttgcaagc cggttgatga cgttgatttt tccgacgttt ggaatgccga taatcaaagc     480
gcgaatcgct ctcggcttca cccttttcgc acgcatccgg tcaaattttt cttggaggat     540
ctcttttgat gcaggcacaa tttgatttaa cccttgtcca tttacagaat taatagacag     600
agagcggatc ccctggttct caaagtgctc tttccactgc tgtgtaactg ccgcatctgc     660
tttgtcagcc ttgtttaaca gcataattcg cggcttgttt tttagaatat cttcaatcat     720
tgggtttctt gatgacattg gaattctggc atctaccaat tcatatacga tatcgattaa     780 ttttaattt tcggttactt cccttcttgc ttttgccata tggcccggga accattgaat     840
tgtcat                                                                 846

<210> SEQ ID NO 19
<211> LENGTH: 516
<212> TYPE: DNA
<213> ORGANISM: Bacillus subtilis
<220> FEATURE:
<221> NAME/KEY: CDS
<222> LOCATION: (1)...(516)

<400> SEQUENCE: 19
```

```
ttg tta aaa aag ttt ttt tta cct gac gag ttt gta aaa aat att ttt    48
Leu Leu Lys Lys Phe Phe Leu Pro Asp Glu Phe Val Lys Asn Ile Phe
 1               5                  10                  15 cat att aca cct gag aaa tta aag gaa cga aat gta aaa gga att att    96
His Ile Thr Pro Glu Lys Leu Lys Glu Arg Asn Val Lys Gly Ile Ile
                20                  25                  30 act gac ctg gat aat acg ctt gtt gaa tgg gac agg ccg aac gcg acg   144
Thr Asp Leu Asp Asn Thr Leu Val Glu Trp Asp Arg Pro Asn Ala Thr
             35                  40                  45 ccg cga ttg atc gag tgg ttt gaa gaa atg aag gaa cac ggc att aaa   192
Pro Arg Leu Ile Glu Trp Phe Glu Glu Met Lys Glu His Gly Ile Lys
         50                  55                  60 gtg aca att gtc tct aat aat aac gaa aga aga gtg aaa ctt ttc tca   240
Val Thr Ile Val Ser Asn Asn Asn Glu Arg Arg Val Lys Leu Phe Ser
 65                  70                  75                  80 gaa ccg ctt gga atc cca ttc atc tat aaa gca aga aaa ccg atg ggt   288
Glu Pro Leu Gly Ile Pro Phe Ile Tyr Lys Ala Arg Lys Pro Met Gly
                 85                  90                  95 aaa gcc ttt aat aga gcg gtg cgc aat atg gag ctg aaa aaa gag gac   336
Lys Ala Phe Asn Arg Ala Val Arg Asn Met Glu Leu Lys Lys Glu Asp
            100                 105                 110 tgc gtt gtc atc gga gac cag ctg ctg acc gat gta ctc ggg gga aac   384
Cys Val Val Ile Gly Asp Gln Leu Leu Thr Asp Val Leu Gly Gly Asn
        115                 120                 125 cga aac ggc tac cat acg att ttg gtc gtg cca gtc gct tcc tct gac   432
Arg Asn Gly Tyr His Thr Ile Leu Val Val Pro Val Ala Ser Ser Asp
130                 135                 140 gga ttc att acg cgc ttt aac cgc cag gtc gaa cgc aga ata ctg agt   480
Gly Phe Ile Thr Arg Phe Asn Arg Gln Val Glu Arg Arg Ile Leu Ser
145                 150                 155                 160 gct ctc aaa cga aaa ggg cac att cag tgg gag gag                   516
Ala Leu Lys Arg Lys Gly His Ile Gln Trp Glu Glu
                165                 170
```

<210> SEQ ID NO 20
<211> LENGTH: 172
<212> TYPE: PRT
<213> ORGANISM: Bacillus subtilis

<400> SEQUENCE: 20

```
Leu Leu Lys Lys Phe Phe Leu Pro Asp Glu Phe Val Lys Asn Ile Phe
 1               5                  10                  15

His Ile Thr Pro Glu Lys Leu Lys Glu Arg Asn Val Lys Gly Ile Ile
                20                  25                  30

Thr Asp Leu Asp Asn Thr Leu Val Glu Trp Asp Arg Pro Asn Ala Thr
             35                  40                  45

Pro Arg Leu Ile Glu Trp Phe Glu Glu Met Lys Glu His Gly Ile Lys
         50                  55                  60

Val Thr Ile Val Ser Asn Asn Asn Glu Arg Arg Val Lys Leu Phe Ser
 65                  70                  75                  80

Glu Pro Leu Gly Ile Pro Phe Ile Tyr Lys Ala Arg Lys Pro Met Gly
                 85                  90                  95

Lys Ala Phe Asn Arg Ala Val Arg Asn Met Glu Leu Lys Lys Glu Asp
            100                 105                 110

Cys Val Val Ile Gly Asp Gln Leu Leu Thr Asp Val Leu Gly Gly Asn
        115                 120                 125

Arg Asn Gly Tyr His Thr Ile Leu Val Val Pro Val Ala Ser Ser Asp
130                 135                 140
```

```
Gly Phe Ile Thr Arg Phe Asn Arg Gln Val Glu Arg Ile Leu Ser
145                 150                 155                 160

Ala Leu Lys Arg Lys Gly His Ile Gln Trp Glu Glu
                165                 170
```

<210> SEQ ID NO 21
<211> LENGTH: 516
<212> TYPE: DNA
<213> ORGANISM: Bacillus subtilis

<400> SEQUENCE: 21

```
ctcctcccac tgaatgtgcc cttttcgttt gagagcactc agtattctgc gttcgacctg    60
gcggttaaag cgcgtaatga atccgtcaga ggaagcgact ggcacgacca aaatcgtatg   120
gtagccgttt cggtttcccc cgagtacatc ggtcagcagc tggtctccga tgacaacgca   180
gtcctctttt ttcagctcca tattgcgcac cgctctatta aaggctttac ccatcggttt   240
tcttgcttta tagatgaatg ggattccaag cggttctgag aaaagtttca ctcttctttc   300
gttattatta gagacaattg tcactttaat gccgtgttcc ttcatttctt caaaccactc   360
gatcaatcgc ggcgtcgcgt tcggcctgtc ccattcaaca agcgtattat ccaggtcagt   420
aataattcct tttacatttc gttcctttaa tttctcaggt gtaatatgaa aaatattttt   480
tacaaactcg tcaggtaaaa aaactttttt taacaa                             516
```

<210> SEQ ID NO 22
<211> LENGTH: 927
<212> TYPE: DNA
<213> ORGANISM: Bacillus subtilis
<220> FEATURE:
<221> NAME/KEY: CDS
<222> LOCATION: (1)...(927)

<400> SEQUENCE: 22

```
atg gaa aag ata ctt att ttc gga cac caa aac cca gat aca gat acg     48
Met Glu Lys Ile Leu Ile Phe Gly His Gln Asn Pro Asp Thr Asp Thr
  1               5                  10                  15 att tgt tct gcg att gct tat gct gat ttg aaa aac aaa ctc ggc ttc     96
Ile Cys Ser Ala Ile Ala Tyr Ala Asp Leu Lys Asn Lys Leu Gly Phe
                 20                  25                  30 aat gct gag cct gtc cgc ctc gga caa gtc aac ggc gaa aca caa tac    144
Asn Ala Glu Pro Val Arg Leu Gly Gln Val Asn Gly Glu Thr Gln Tyr
             35                  40                  45 gcg ctt gac tat ttc aaa caa gaa agc ccg cgt ctt gtt gaa aca gct    192
Ala Leu Asp Tyr Phe Lys Gln Glu Ser Pro Arg Leu Val Glu Thr Ala
         50                  55                  60 gca aac gaa gta aac ggc gtt atc ctg gtt gac cat aac gaa cgc cag    240
Ala Asn Glu Val Asn Gly Val Ile Leu Val Asp His Asn Glu Arg Gln
 65                  70                  75                  80 caa agc atc aaa gac att gaa gag gtt cag gtt tta gag gtt atc gac    288
Gln Ser Ile Lys Asp Ile Glu Glu Val Gln Val Leu Glu Val Ile Asp
                 85                  90                  95 cat cac cgc atc gct aac ttt gaa aca gct gag ccg ctt tac tat cgt    336
His His Arg Ile Ala Asn Phe Glu Thr Ala Glu Pro Leu Tyr Tyr Arg
            100                 105                 110 gct gag cct gta ggc tgt acg gct acc atc tta aac aaa atg tac aaa    384
Ala Glu Pro Val Gly Cys Thr Ala Thr Ile Leu Asn Lys Met Tyr Lys
        115                 120                 125 gag aat aac gtg aaa atc gag aaa gaa att gcc ggc ctt atg ctg tct    432
Glu Asn Asn Val Lys Ile Glu Lys Glu Ile Ala Gly Leu Met Leu Ser
    130                 135                 140
```

-continued

| | | |
|---|---|---|
| gcg atc att tct gat tcc ctg tta ttt aaa tct cca act tgc acg gac<br>Ala Ile Ile Ser Asp Ser Leu Leu Phe Lys Ser Pro Thr Cys Thr Asp<br>145                       150                        155                      160 | 480 |
| caa gac gta gca gca gca aaa gag ctt gcg gag atc gct gga gta gat<br>Gln Asp Val Ala Ala Ala Lys Glu Leu Ala Glu Ile Ala Gly Val Asp<br>                        165                        170                     175 | 528 |
| gct gaa gaa tac ggc ttg aac atg ttg aaa gca ggc gct gat cta agc<br>Ala Glu Glu Tyr Gly Leu Asn Met Leu Lys Ala Gly Ala Asp Leu Ser<br>                  180                        185                     190 | 576 |
| aaa aaa aca gtg gaa gag ctc att tct ctt gat gcg aaa gaa ttt aca<br>Lys Lys Thr Val Glu Glu Leu Ile Ser Leu Asp Ala Lys Glu Phe Thr<br>          195                        200                     205 | 624 |
| ctc ggc agc aag aaa gtc gaa atc gca caa gta aac aca gtg gac att<br>Leu Gly Ser Lys Lys Val Glu Ile Ala Gln Val Asn Thr Val Asp Ile<br>          210                        215                     220 | 672 |
| gaa gat gta aaa aaa cgc caa gct gaa tta gaa gct gtg atc tca aaa<br>Glu Asp Val Lys Lys Arg Gln Ala Glu Leu Glu Ala Val Ile Ser Lys<br>225                       230                        235                     240 | 720 |
| gtt gtg gct gag aag aat ctt gat ctg ttc ctt ctc gtt atc aca gat<br>Val Val Ala Glu Lys Asn Leu Asp Leu Phe Leu Leu Val Ile Thr Asp<br>                  245                        250                     255 | 768 |
| atc tta gaa aat gat tca ctt gct ctt gca atc ggt aac gaa gca gcg<br>Ile Leu Glu Asn Asp Ser Leu Ala Leu Ala Ile Gly Asn Glu Ala Ala<br>                260                        265                     270 | 816 |
| aaa gtg gaa aaa gcg ttc aac gtt aca tta gaa aac aac aca gcc ctc<br>Lys Val Glu Lys Ala Phe Asn Val Thr Leu Glu Asn Asn Thr Ala Leu<br>          275                        280                     285 | 864 |
| tta aaa ggc gtt gtt tcc cgt aaa aaa caa gtc gtt cct gtc tta aca<br>Leu Lys Gly Val Val Ser Arg Lys Lys Gln Val Val Pro Val Leu Thr<br>          290                        295                     300 | 912 |
| gac gca atg gct gaa<br>Asp Ala Met Ala Glu<br>305 | 927 |

<210> SEQ ID NO 23
<211> LENGTH: 309
<212> TYPE: PRT
<213> ORGANISM: Bacillus subtilis

<400> SEQUENCE: 23

Met Glu Lys Ile Leu Ile Phe Gly His Gln Asn Pro Asp Thr Asp Thr
1               5                   10                  15

Ile Cys Ser Ala Ile Ala Tyr Ala Asp Leu Lys Asn Lys Leu Gly Phe
              20                   25                     30

Asn Ala Glu Pro Val Arg Leu Gly Gln Val Asn Gly Glu Thr Gln Tyr
          35                        40                     45

Ala Leu Asp Tyr Phe Lys Gln Glu Ser Pro Arg Leu Val Glu Thr Ala
    50                   55                   60

Ala Asn Glu Val Asn Gly Val Ile Leu Val Asp His Asn Glu Arg Gln
65                     70                   75                  80

Gln Ser Ile Lys Asp Ile Glu Glu Val Gln Val Leu Glu Val Ile Asp
              85                   90                  95

His His Arg Ile Ala Asn Phe Glu Thr Ala Glu Pro Leu Tyr Tyr Arg
         100                     105                   110

Ala Glu Pro Val Gly Cys Thr Ala Thr Ile Leu Asn Lys Met Tyr Lys
        115                     120                   125

Glu Asn Asn Val Lys Ile Glu Lys Glu Ile Ala Gly Leu Met Leu Ser
     130                    135                   140

-continued

```
Ala Ile Ile Ser Asp Ser Leu Leu Phe Lys Ser Pro Thr Cys Thr Asp
145                 150                 155                 160

Gln Asp Val Ala Ala Lys Glu Leu Ala Glu Ile Ala Gly Val Asp
            165                 170                 175

Ala Glu Glu Tyr Gly Leu Asn Met Leu Lys Ala Gly Ala Asp Leu Ser
            180                 185                 190

Lys Lys Thr Val Glu Glu Leu Ile Ser Leu Asp Ala Lys Glu Phe Thr
            195                 200                 205

Leu Gly Ser Lys Lys Val Glu Ile Ala Gln Val Asn Thr Val Asp Ile
    210                 215                 220

Glu Asp Val Lys Lys Arg Gln Ala Glu Leu Ala Val Ile Ser Lys
225                 230                 235                 240

Val Val Ala Glu Lys Asn Leu Asp Leu Phe Leu Leu Val Ile Thr Asp
                245                 250                 255

Ile Leu Glu Asn Asp Ser Leu Ala Leu Ala Ile Gly Asn Glu Ala Ala
            260                 265                 270

Lys Val Glu Lys Ala Phe Asn Val Thr Leu Glu Asn Asn Thr Ala Leu
            275                 280                 285

Leu Lys Gly Val Val Ser Arg Lys Lys Gln Val Val Pro Val Leu Thr
    290                 295                 300

Asp Ala Met Ala Glu
305
```

<210> SEQ ID NO 24
<211> LENGTH: 927
<212> TYPE: DNA
<213> ORGANISM: Bacillus subtilis

<400> SEQUENCE: 24

```
ttcagccatt gcgtctgtta agacaggaac gacttgtttt ttacgggaaa caacgccttt      60
taagagggct gtgttgtttt ctaatgtaac gttgaacgct ttttccactt tcgctgcttc     120
gttaccgatt gcaagagcaa gtgaatcatt ttctaagata tctgtgataa cgagaaggaa     180
cagatcaaga ttcttctcag ccacaacttt tgagatcaca gcttctaatt cagcttggcg     240
tttttttaca tcttcaatgt ccactgtgtt tacttgtgcg atttcgactt tcttgctgcc     300
gagtgtaaat tctttcgcat caagagaaat gagctcttcc actgtttttt tgcttagatc     360
agcgcctgct ttcaacatgt tcaagccgta ttcttcagca tctactccag cgatctccgc     420
aagctctttt gctgctgcta cgtcttggtc cgtgcaagtt ggagatttaa ataacaggga     480
atcagaaatg atcgcagaca gcataaggcc ggcaatttct ttctcgattt tcacgttatt     540
ctctttgtac attttgttta agatggtagc cgtacagcct acaggctcag cacgatagta     600
aagcggctca gctgtttcaa agttagcgat gcggtgatgg tcgataacct ctaaaacctg     660
aacctcttca atgtctttga tgctttgctg gcgttcgtta tggtcaacca ggataacgcc     720
gtttacttcg tttgcagctg tttcaacaag acgcgggctt tcttgtttga aatagtcaag     780
cgcgtattgt gtttcgccgt tgacttgtcc gaggcggaca ggctcagcat tgaagccgag     840
tttgttttc aaatcagcat aagcaatcgc agaacaaatc gtatctgtat ctgggttttg     900
gtgtccgaaa ataagtatct tttccat                                        927
```

<210> SEQ ID NO 25
<211> LENGTH: 288
<212> TYPE: DNA
<213> ORGANISM: Bacillus subtilis
<220> FEATURE:

<221> NAME/KEY: CDS
<222> LOCATION: (1)...(288)

<400> SEQUENCE: 25

| | | | | | | | | | | | | | | | | |
|---|---|---|---|---|---|---|---|---|---|---|---|---|---|---|---|---|
| atg | tca | cga | att | tca | ata | gaa | gaa | gta | aag | cac | gtt | gcg | cac | ctt | gca | 48 |
| Met | Ser | Arg | Ile | Ser | Ile | Glu | Glu | Val | Lys | His | Val | Ala | His | Leu | Ala | |
| 1 | | | | 5 | | | | | 10 | | | | | 15 | | |
| aga | ctt | gcg | att | act | gaa | gaa | gaa | gca | aaa | atg | ttc | act | gaa | cag | ctc | 96 |
| Arg | Leu | Ala | Ile | Thr | Glu | Glu | Glu | Ala | Lys | Met | Phe | Thr | Glu | Gln | Leu | |
| | | | | 20 | | | | | 25 | | | | | 30 | | |
| gac | agt | atc | att | tca | ttt | gcc | gag | gag | ctt | aat | gag | gtt | aac | aca | gac | 144 |
| Asp | Ser | Ile | Ile | Ser | Phe | Ala | Glu | Glu | Leu | Asn | Glu | Val | Asn | Thr | Asp | |
| | | 35 | | | | | 40 | | | | | 45 | | | | |
| aat | gtg | gag | cct | aca | act | cac | gtg | ctg | aaa | atg | aaa | aat | gtc | atg | aga | 192 |
| Asn | Val | Glu | Pro | Thr | Thr | His | Val | Leu | Lys | Met | Lys | Asn | Val | Met | Arg | |
| | 50 | | | | | 55 | | | | | 60 | | | | | |
| gaa | gat | gaa | gcg | ggt | aaa | ggt | ctt | ccg | gtt | gag | gat | gtc | atg | aaa | aat | 240 |
| Glu | Asp | Glu | Ala | Gly | Lys | Gly | Leu | Pro | Val | Glu | Asp | Val | Met | Lys | Asn | |
| 65 | | | | | 70 | | | | | 75 | | | | | 80 | |
| gcg | cct | gac | cat | aaa | gac | ggc | tat | att | cgt | gtg | cca | tca | att | ctg | gac | 288 |
| Ala | Pro | Asp | His | Lys | Asp | Gly | Tyr | Ile | Arg | Val | Pro | Ser | Ile | Leu | Asp | |
| | | | | 85 | | | | | 90 | | | | | 95 | | |

<210> SEQ ID NO 26
<211> LENGTH: 96
<212> TYPE: PRT
<213> ORGANISM: Bacillus subtilis

<400> SEQUENCE: 26

Met Ser Arg Ile Ser Ile Glu Glu Val Lys His Val Ala His Leu Ala
1               5                   10                  15

Arg Leu Ala Ile Thr Glu Glu Glu Ala Lys Met Phe Thr Glu Gln Leu
            20                  25                  30

Asp Ser Ile Ile Ser Phe Ala Glu Glu Leu Asn Glu Val Asn Thr Asp
        35                  40                  45

Asn Val Glu Pro Thr Thr His Val Leu Lys Met Lys Asn Val Met Arg
    50                  55                  60

Glu Asp Glu Ala Gly Lys Gly Leu Pro Val Glu Asp Val Met Lys Asn
65                  70                  75                  80

Ala Pro Asp His Lys Asp Gly Tyr Ile Arg Val Pro Ser Ile Leu Asp
                85                  90                  95

<210> SEQ ID NO 27
<211> LENGTH: 288
<212> TYPE: DNA
<213> ORGANISM: Bacillus subtilis

<400> SEQUENCE: 27
gtccagaatt gatggcacac gaatatagcc gtctttatgg tcaggcgcat ttttcatgac      60
atcctcaacc ggaagacctt tacccgcttc atcttctctc atgacatttt tcattttcag     120
cacgtgagtt gtaggctcca cattgtctgt gttaacctca ttaagctcct cggcaaatga     180
aatgatactg tcgagctgtt cagtgaacat ttttgcttct tcttcagtaa tcgcaagtct     240
tgcaaggtgc gcaacgtgct ttacttcttc tattgaaatt cgtgacat                 288

<210> SEQ ID NO 28
<211> LENGTH: 585
<212> TYPE: DNA
<213> ORGANISM: Bacillus subtilis
<220> FEATURE:

```
<221> NAME/KEY: CDS
<222> LOCATION: (1)...(585)

<400> SEQUENCE: 28 atg aaa gtc aca aag tca gaa atc gtg atc agt gca gta aaa ccg gaa      48
Met Lys Val Thr Lys Ser Glu Ile Val Ile Ser Ala Val Lys Pro Glu
 1               5                  10                  15 cag tac cct gaa ggg ggg ctt ccg gaa atc gca ttg gcc gga aga tcg      96
Gln Tyr Pro Glu Gly Gly Leu Pro Glu Ile Ala Leu Ala Gly Arg Ser
             20                  25                  30 aac gta gga aaa tcg tct ttt atc aat tca tta atc aat cgc aaa aat     144
Asn Val Gly Lys Ser Ser Phe Ile Asn Ser Leu Ile Asn Arg Lys Asn
         35                  40                  45 ctt gcg aga acg tca tca aag ccg gga aaa aca caa acg ctt aat ttc     192
Leu Ala Arg Thr Ser Ser Lys Pro Gly Lys Thr Gln Thr Leu Asn Phe
 50                  55                  60 tac att atc aat gat gag ctg cat ttt gtg gat gtg ccg ggc tac ggt     240
Tyr Ile Ile Asn Asp Glu Leu His Phe Val Asp Val Pro Gly Tyr Gly
 65                  70                  75                  80 ttt gcc aaa gtg tca aag tct gag cgt gaa gca tgg ggc aga atg att     288
Phe Ala Lys Val Ser Lys Ser Glu Arg Glu Ala Trp Gly Arg Met Ile
                 85                  90                  95 gaa acc tat atc acg aca cgc gag gaa tta aaa gct gtg gtg cag atc     336
Glu Thr Tyr Ile Thr Thr Arg Glu Glu Leu Lys Ala Val Val Gln Ile
            100                 105                 110 gtt gat ttg cgg cat gcg cca tct aat gat gat gta cag atg tat gaa     384
Val Asp Leu Arg His Ala Pro Ser Asn Asp Asp Val Gln Met Tyr Glu
        115                 120                 125 ttt tta aag tat tac ggc att cct gtt att gtt atc gct aca aag gcg     432
Phe Leu Lys Tyr Tyr Gly Ile Pro Val Ile Val Ile Ala Thr Lys Ala
130                 135                 140 gat aag atc ccg aaa ggt aaa tgg gac aaa cac gcg aag gtt gtc cga     480
Asp Lys Ile Pro Lys Gly Lys Trp Asp Lys His Ala Lys Val Val Arg
145                 150                 155                 160 caa aca tta aat att gat ccg gaa gac gag ctg atc ctc ttt tct tca     528
Gln Thr Leu Asn Ile Asp Pro Glu Asp Glu Leu Ile Leu Phe Ser Ser
                165                 170                 175 gaa acg aaa aag gga aaa gac gaa gct tgg gga gca atc aaa aaa atg     576
Glu Thr Lys Lys Gly Lys Asp Glu Ala Trp Gly Ala Ile Lys Lys Met
            180                 185                 190 ata aac cgg                                                          585
Ile Asn Arg
        195

<210> SEQ ID NO 29
<211> LENGTH: 195
<212> TYPE: PRT
<213> ORGANISM: Bacillus subtilis

<400> SEQUENCE: 29

Met Lys Val Thr Lys Ser Glu Ile Val Ile Ser Ala Val Lys Pro Glu
 1               5                  10                  15

Gln Tyr Pro Glu Gly Gly Leu Pro Glu Ile Ala Leu Ala Gly Arg Ser
             20                  25                  30

Asn Val Gly Lys Ser Ser Phe Ile Asn Ser Leu Ile Asn Arg Lys Asn
         35                  40                  45

Leu Ala Arg Thr Ser Ser Lys Pro Gly Lys Thr Gln Thr Leu Asn Phe
 50                  55                  60

Tyr Ile Ile Asn Asp Glu Leu His Phe Val Asp Val Pro Gly Tyr Gly
 65                  70                  75                  80
```

Phe Ala Lys Val Ser Lys Ser Glu Arg Glu Ala Trp Gly Arg Met Ile
            85                  90                  95

Glu Thr Tyr Ile Thr Thr Arg Glu Glu Leu Lys Ala Val Val Gln Ile
        100                 105                 110

Val Asp Leu Arg His Ala Pro Ser Asn Asp Val Gln Met Tyr Glu
    115                 120                 125

Phe Leu Lys Tyr Tyr Gly Ile Pro Val Ile Val Ala Thr Lys Ala
    130                 135                 140

Asp Lys Ile Pro Lys Gly Lys Trp Asp Lys His Ala Lys Val Val Arg
145                 150                 155                 160

Gln Thr Leu Asn Ile Asp Pro Glu Asp Glu Leu Ile Leu Phe Ser Ser
            165                 170                 175

Glu Thr Lys Lys Gly Lys Asp Glu Ala Trp Gly Ala Ile Lys Lys Met
            180                 185                 190

Ile Asn Arg
        195

<210> SEQ ID NO 30
<211> LENGTH: 585
<212> TYPE: DNA
<213> ORGANISM: Bacillus subtilis

<400> SEQUENCE: 30
ccggtttatc attttttga tcgctcccca agcttcgtct tttcccttt tcgtttctga      60 agaaaagagg atcagctcgt cttccggatc aatatttaat gtttgtcgga caaccttcgc  120
gtgtttgtcc catttacctt tcgggatctt atccgccttt gtagcgataa caataacagg  180
aatgccgtaa tactttaaaa attcatacat ctgtacatca tcattagatg gcgcatgccg  240
caaatcaacg atctgcacca cagcttttaa ttcctcgcgt gtcgtgatat aggtttcaat  300
cattctgccc catgcttcac gctcagactt tgacactttg caaaaccgt agcccggcac   360 atccacaaaa tgcagctcat cattgataat gtagaaatta agcgtttgtg ttttcccgg   420 ctttgatgac gttctcgcaa gattttgcg attgattaat gaattgataa agacgattt    480 tcctacgttc gatcttccgg ccaatgcgat ttccggaagc cccccttcag ggtactgttc  540
cggttttact gcactgatca cgatttctga ctttgtgact ttcat                  585

<210> SEQ ID NO 31
<211> LENGTH: 21
<212> TYPE: DNA
<213> ORGANISM: Artificial Sequence
<220> FEATURE:
<223> OTHER INFORMATION: synthetically generated primer

<400> SEQUENCE: 31
gtgttcgtgc tgacttgcac c                                             21

<210> SEQ ID NO 32
<211> LENGTH: 21
<212> TYPE: DNA
<213> ORGANISM: Artificial Sequence
<220> FEATURE:
<223> OTHER INFORMATION: synthetically generated primer

<400> SEQUENCE: 32
gaattatttc ctcccgttaa a                                             21

<210> SEQ ID NO 33

```
<211> LENGTH: 21
<212> TYPE: DNA
<213> ORGANISM: Artificial Sequence
<220> FEATURE:
<223> OTHER INFORMATION: synthetically generated primer

<400> SEQUENCE: 33
gaaaagtcat catttgatgg c                                          21

<210> SEQ ID NO 34
<211> LENGTH: 42
<212> TYPE: DNA
<213> ORGANISM: Artificial Sequence
<220> FEATURE:
<223> OTHER INFORMATION: synthetically generated primer

<400> SEQUENCE: 34
ggtgcaagtc agcacgaaca cctagataga ggcaagcgtg ca                    42

<210> SEQ ID NO 35
<211> LENGTH: 42
<212> TYPE: DNA
<213> ORGANISM: Artificial Sequence
<220> FEATURE:
<223> OTHER INFORMATION: synthetically generated primer

<400> SEQUENCE: 35
tttaacggga ggaaataatt cgtctcttcg tgaaggaagt cc                    42

<210> SEQ ID NO 36
<211> LENGTH: 21
<212> TYPE: DNA
<213> ORGANISM: Artificial Sequence
<220> FEATURE:
<223> OTHER INFORMATION: synthetically generated primer

<400> SEQUENCE: 36
ctgtgccata tcctgcatta g                                          21

<210> SEQ ID NO 37
<211> LENGTH: 21
<212> TYPE: DNA
<213> ORGANISM: Artificial Sequence
<220> FEATURE:
<223> OTHER INFORMATION: synthetically generated primer

<400> SEQUENCE: 37
cttgctctat atcagtttgg c                                          21

<210> SEQ ID NO 38
<211> LENGTH: 42
<212> TYPE: DNA
<213> ORGANISM: Artificial Sequence
<220> FEATURE:
<223> OTHER INFORMATION: synthetically generated primer

<400> SEQUENCE: 38
ggtgcaagtc agcacgaaca cggttgttcc aagcaatgag gg                    42

<210> SEQ ID NO 39
<211> LENGTH: 42
<212> TYPE: DNA
<213> ORGANISM: Artificial Sequence
<220> FEATURE:
<223> OTHER INFORMATION: synthetically generated primer

<400> SEQUENCE: 39
```

```
tttaacggga ggaaataatt catcactgaa aagtacggac cg                          42

<210> SEQ ID NO 40
<211> LENGTH: 21
<212> TYPE: DNA
<213> ORGANISM: Artificial Sequence
<220> FEATURE:
<223> OTHER INFORMATION: synthetically generated primer

<400> SEQUENCE: 40
ttaagctgat agctcttagg c                                                 21

<210> SEQ ID NO 41
<211> LENGTH: 21
<212> TYPE: DNA
<213> ORGANISM: Artificial Sequence
<220> FEATURE:
<223> OTHER INFORMATION: synthetically generated primer

<400> SEQUENCE: 41
agcgcctgca gtttgtttat c                                                 21

<210> SEQ ID NO 42
<211> LENGTH: 42
<212> TYPE: DNA
<213> ORGANISM: Artificial Sequence
<220> FEATURE:
<223> OTHER INFORMATION: synthetically generated primer

<400> SEQUENCE: 42
ggtgcaagtc agcacgaaca ccagatgacc cgatggcatc tg                          42

<210> SEQ ID NO 43
<211> LENGTH: 42
<212> TYPE: DNA
<213> ORGANISM: Artificial Sequence
<220> FEATURE:
<223> OTHER INFORMATION: synthetically generated primer

<400> SEQUENCE: 43
tttaacggga ggaaataatt cgacaaggtc gaagcggctt tc                          42

<210> SEQ ID NO 44
<211> LENGTH: 21
<212> TYPE: DNA
<213> ORGANISM: Artificial Sequence
<220> FEATURE:
<223> OTHER INFORMATION: synthetically generated primer

<400> SEQUENCE: 44
ctgggagcag tagaaaccag c                                                 21

<210> SEQ ID NO 45
<211> LENGTH: 21
<212> TYPE: DNA
<213> ORGANISM: Artificial Sequence
<220> FEATURE:
<223> OTHER INFORMATION: synthetically generated primer

<400> SEQUENCE: 45
gtcctcgtgc cctggcgtgt c                                                 21

<210> SEQ ID NO 46
<211> LENGTH: 42
<212> TYPE: DNA
```

```
<213> ORGANISM: Artificial Sequence
<220> FEATURE:
<223> OTHER INFORMATION: synthetically generated primer

<400> SEQUENCE: 46
ggtgcaagtc agcacgaaca cggcaacgtg tgttacctct tc                          42

<210> SEQ ID NO 47
<211> LENGTH: 42
<212> TYPE: DNA
<213> ORGANISM: Artificial Sequence
<220> FEATURE:
<223> OTHER INFORMATION: synthetically generated primer

<400> SEQUENCE: 47
tttaacggga ggaaataatt cctagacaat ggaggagatg cc                          42

<210> SEQ ID NO 48
<211> LENGTH: 21
<212> TYPE: DNA
<213> ORGANISM: Artificial Sequence
<220> FEATURE:
<223> OTHER INFORMATION: synthetically generated primer

<400> SEQUENCE: 48
aggttggcgg atggaaccac c                                                 21

<210> SEQ ID NO 49
<211> LENGTH: 20
<212> TYPE: DNA
<213> ORGANISM: Artificial Sequence
<220> FEATURE:
<223> OTHER INFORMATION: synthetically generated primer

<400> SEQUENCE: 49
ctgttgctag gtaccgcctc                                                   20

<210> SEQ ID NO 50
<211> LENGTH: 41
<212> TYPE: DNA
<213> ORGANISM: Artificial Sequence
<220> FEATURE:
<223> OTHER INFORMATION: synthetically generated primer

<400> SEQUENCE: 50
ggtgcaagtc agcacgaaca ccctgcggat agtgggactt a                           41

<210> SEQ ID NO 51
<211> LENGTH: 41
<212> TYPE: DNA
<213> ORGANISM: Artificial Sequence
<220> FEATURE:
<223> OTHER INFORMATION: synthetically generated primer

<400> SEQUENCE: 51
tttaacggga ggaaataatt ctgacccaag tgacgatttc a                           41

<210> SEQ ID NO 52
<211> LENGTH: 20
<212> TYPE: DNA
<213> ORGANISM: Artificial Sequence
<220> FEATURE:
<223> OTHER INFORMATION: synthetically generated primer
```

```
<400> SEQUENCE: 52
ccagctgcaa aaacttaggc                                                    20
```

What is claimed is:

1. A method for determining whether a test compound is a candidate antibacterial agent, the method comprising:

(a) contacting the test compound with a polypeptide selected from the group consisting of S-yqeG (SEQ ID NO:5), B-yqeG (SEQ ID NO:20); S-yybQ (SEQ ID NO:8); and B-yybQ (SEQ ID NO:23); and (b) detecting binding of the test compound with the polypeptide, wherein binding indicates that the test compound is a candidate antibacterial agent.

2. A method of claim 1, further comprising:

(c) determining whether the candidate antibacterial agent inhibits growth of bacteria, relative to growth of bacteria cultured in the absence of a test compound that binds to the polypeptide, wherein inhibition of growth indicates that the candidate antibacterial agent is an antibacterial agent.

3. A method of claim 1, wherein the polypeptide is isolated from a non-pathogenic Streptococcus strain.

4. A method of claim 1, wherein the polypeptide is isolated from a pathogenic Streptococcus strain.

* * * * *

UNITED STATES PATENT AND TRADEMARK OFFICE
CERTIFICATE OF CORRECTION

PATENT NO. : 6,815,177 B2
DATED : November 9, 2004
INVENTOR(S) : Christian Fritz, Philip Youngman and Luz-Maria Guzman It is certified that error appears in the above-identified patent and that said Letters Patent is hereby corrected as shown below:

Column 68,
Line 16, after "pathogenic Streptococcus strain." insert -- 5. A method of claim 1, wherein the test compound is immobilized on a substrate, and binding of the test compound with the polypeptide is detected as immobilization of the polypeptide on the immobilized test compound.

6. A method of claim 1, wherein the test compound is selected from the group consisting of polypeptides and small organic molecules.

7. A method of claim 1, wherein the S-yqeG, B-yqeG, S-yybQ or B-yybQ polypeptide is provided as a first fusion protein comprising the polypeptide fused to (i) a transcription activation domain of a transcription factor or (ii) a DNA-binding domain of a transcription factor;
 the test compound is provided as a second fusion protein comprising a test polypeptide fused to (i) a transcription activation domain of a transcription factor or (ii) a DNA-binding domain of a transcription factor, wherein the first and second fusion proteins comprise different domains of the transcription factor to enable the second fusion protein to interact with the first fusion protein; and wherein
 binding of the test polypeptide with the S-yqeG, B-yqeG, S-yybQ or B-yybQ polypeptide brings the transcription activation domain and the DNA-binding domain together to reconstitute a functional transcription factor. --.

Signed and Sealed this

Twenty-first Day of February, 2006

JON W. DUDAS
*Director of the United States Patent and Trademark Office*